United States Patent
Watanabe et al.

(10) Patent No.: US 7,157,286 B2
(45) Date of Patent: Jan. 2, 2007

(54) METHOD FOR IMMUNOLOGICALLY MEASURING RCAS1 AND KIT FOR MEASURING THE SAME

(75) Inventors: Takeshi Watanabe, Fukuoka (JP); Manabu Nakashima, Fukuoka (JP); Kenzo Sonoda, Fukuoka (JP)

(73) Assignee: Medical & Biological Laboratories Co., Ltd. (JP)

( * ) Notice: Subject to any disclaimer, the term of this patent is extended or adjusted under 35 U.S.C. 154(b) by 621 days.

(21) Appl. No.: 10/155,041

(22) Filed: May 24, 2002

(65) Prior Publication Data

US 2003/0022259 A1    Jan. 30, 2003

Related U.S. Application Data

(63) Continuation-in-part of application No. 09/627,137, filed on Jul. 27, 2000, now abandoned.

(30) Foreign Application Priority Data

Jan. 31, 2000   (JP)   ............................... 2000-22706

(51) Int. Cl.
    *G01N 33/543*   (2006.01)

(52) U.S. Cl. .................. 436/501; 436/518; 435/7.1; 435/7.23

(58) Field of Classification Search ................ 436/501, 436/518; 435/7.23, 7.72, 7.92, 7.93
    See application file for complete search history.

(56) References Cited

OTHER PUBLICATIONS

Sonoda et al., Cancer. Apr. 15, 1996;77(8):1501-9.*
Nakashima et al., Aug. 1999, Nature Medicine, vol. 5, pp. 938-942.*
Bouche et al., Journal of Clinical Microbiology, Mar. 1998, p. 721-726, vol. 36, No. 3.*
Harlow et al., Antibodies, A Laboratory Manual, 1998, Cold Spring Harbor Laboratory, p. 558 only.*

* cited by examiner

*Primary Examiner*—Misook Yu
(74) *Attorney, Agent, or Firm*—Welsh & Katz, Ltd.; Thomas W. Tolpin

(57) ABSTRACT

RCAS1 in a specimen is measured by a immunologically method consisting of a step of reacting a specimen with a first anti-RCAS1 antibody capable of specifically binding to RCAS1, a step of labeling the first reaction product produced by the aforementioned step, and a step of measuring a labeled amount of the labeled first reaction product. As RCAS1, recombinant RCAS1 is used. In addition, as a first anti-RCAS1, a monoclonal antibody derived from the SiSo cell line is used.

6 Claims, 18 Drawing Sheets

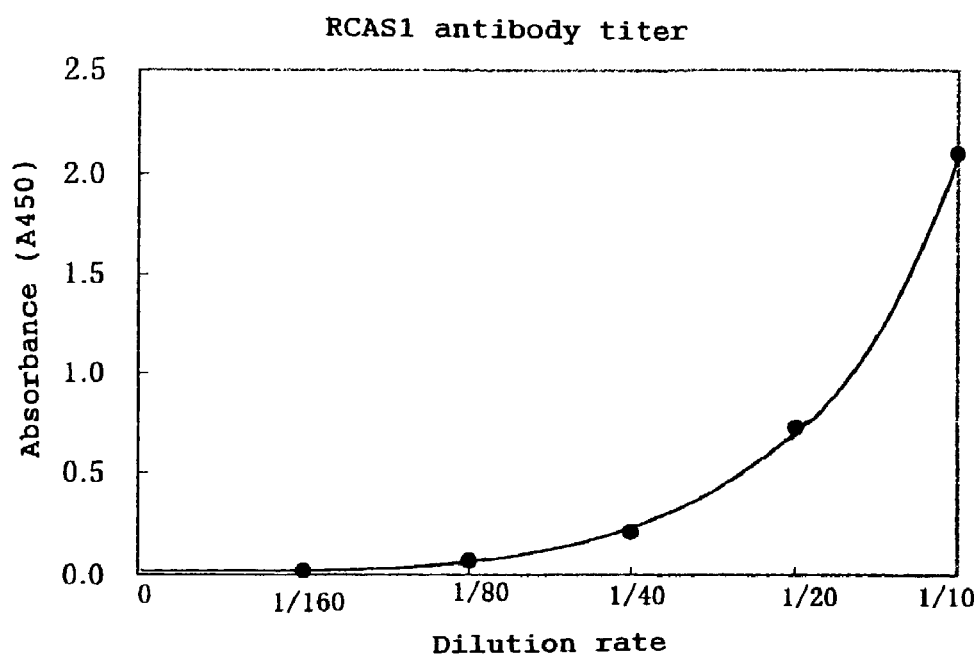
F I G. 1

| Specimen | Measured value (U/mL) | Specimen | Measured value (U/mL) |
|---|---|---|---|
| Healthy subject 1 | 20.3 | Ovary cancer 1 | 47.7 |
| Healthy subject 2 | 19.6 | Ovary cancer 2 | 106.8 |
| Healthy subject 3 | 21.2 | Ovary cancer 3 | 54.8 |
| Healthy subject 4 | 22.8 | Ovary cancer 4 | 44.8 |
| Healthy subject 5 | 20.1 | Ovary cancer 5 | 76.2 |
| Healthy subject 6 | 20.5 | Esophageal planocellular cancer 1 | 58.9 |
| Healthy subject 7 | 23.8 | Esophageal planocellular cancer 2 | 81.5 |
| Healthy subject 8 | 15.6 | Gastric cancer 1 | 77.2 |
| Healthy subject 9 | 30.6 | Gastric cancer 2 | 71.3 |
| Healthy subject 10 | 28.7 | Gastric cancer 3 | 83.8 |
| Uterine neck cancer 1 | 88.3 | Colonic cancer 1 | 43.7 |
| Uterine neck cancer 2 | 128.5 | Colonic cancer 2 | 33.0 |
| Uterine neck cancer 3 | 50.9 | Colonic cancer 3 | 57.8 |
| Uterine neck cancer 4 | 31.3 | Pancreatic cancer 1 | 65.6 |
| Uterine neck cancer 5 | 64.2 | Pancreatic cancer 2 | 81.2 |
| Uterine neck cancer 6 | 44.8 | Heteromorphism 1 | 30.6 |
| Uterine neck cancer 7 | 39.8 | Heteromorphism 2 | 28.5 |
| Uterine neck cancer 8 | 56.7 | Heteromorphism 3 | 16.7 |
| Uterine neck cancer 9 | 84.7 | Heteromorphism 4 | 33.7 |

FIG. 3

```
  1
5' ATG GCC ATC ACC CAG TTT CGG TTA TTT AAA TTT TGT ACC TGC CTA GCA ACA GTA
    M   A   I   T   Q   F   R   L   F   K   F   C   T   C   L   A   T   V

55
   TTC TCA TTC CTA AAG AGA TTA ATA TGC AGA TCT GGC AGA GGA CGG AAA TTA AGT
    F   S   F   L   K   R   L   I   C   R   S   G   R   G   R   K   L   S

109
   GGA GAC CAA ATA ACT TTG CCA ACT ACA GTT GAT TAT TCA TCA GTT CCT AAG CAG
    G   D   Q   I   T   L   P   T   T   V   D   Y   S   S   V   P   K   Q

163
   ACA GAT GTT GAA GAG TGG ACT TCC TGG GAT GAA GAT GCA CCC ACC AGT GTA AAG
    T   D   V   E   E   W   T   S   W   D   E   D   A   P   T   S   V   K

217
   ATC GAA GGA GGG AAT GGG AAT GTG GCA ACA CAA CAA AAT TCT TTG GAA CAA CTG
    I   E   G   G   N   G   N   V   A   T   Q   Q   N   S   L   E   Q   L

271
   GAA CCT GAC TAT TTT AAG GAC ATG ACA CCA ACT ATT AGG AAA ACT CAG AAA ATT
    E   P   D   Y   F   K   D   M   T   P   T   I   R   K   T   Q   K   I

325
   GTT ATT AAG AAG AGA GAA CCA TTG AAT TTT GGC ATC CCA GAT GGG AGC ACA GGT
    V   I   K   K   R   E   P   L   N   F   G   I   P   D   G   S   T   G

379
   TTC TCT AGT AGA TTA GCA GCT ACA CAA GAT CTG CCT TTT ATT CAT CAG TCT TCT
    F   S   S   R   L   A   A   T   Q   D   L   P   F   I   H   Q   S   S

433
   GAA TTA GGT GAC TTA GAT ACC TGG CAG GAA AAT ACC AAT GCA TGG GAA GAA GAA
    E   L   G   D   L   D   T   W   Q   E   N   T   N   A   W   E   E   E

487
   GAA GAT GCA GCC TGG CAA GCA GAA GAA GTT CTG AGA CAG CAG AAA CTA GCA GAC
    E   D   A   A   W   Q   A   E   E   V   L   R   Q   Q   K   L   A   D

541
   AGA GAA AAG AGA GCA GCC GAA CAA CAA AGG AAG AAA ATG GAA AAG GAA GCA CAA
    R   E   K   R   A   A   E   Q   Q   R   K   K   M   E   K   E   A   Q 595                                                                  639
   CGG CTA ATG AAG AAG GAA CAA AAC AAA ATT GGT GTG AAA CTT TCA TAA 3'
    R   L   M   K   K   E   Q   N   K   I   G   V   K   L   S   *
```

FIG. 6

| OD450/620 | | | |
|---|---|---|---|
| Specimen | No sialidase treatment | Sialidase treatment | Treatment/ No treatment |
| Pulmonary cancer 1-1 | 0.034 | 1.196 | 3517.6% |
| Pulmonary cancer 1-5 | 0.190 | 2.363 | 1243.7% |
| Pulmonary cancer 1-9 | 1.057 | 2.383 | 225.4% |
| Ovarian cancer 2-4 | 0.269 | 1.370 | 509.3% |
| Ovarian cancer 2-2 | 0.014 | 0.104 | 742.9% |
| Ovarian cancer 2-7 | 0.127 | 2.205 | 1736.2% |
| Colonic cancer 3-10 | 0.033 | 0.941 | 2851.5% |
| Colonic cancer 3-6 | 0.027 | 1.766 | 6540.7% |
| Colonic cancer 3-5 | 0.075 | 2.067 | 2756.0% |
| Colonic cancer 3-9 | 0.121 | 1.971 | 1628.9% |
| Colonic cancer 3-4 | 0.097 | 2.227 | 2295.9% |
| Breast cancer 5-1 | 0.025 | 0.665 | 2660.0% |
| Pulmonary cancer 1 | 0.014 | 0.141 | 1007.1% |
| Pulmonary cancer 2 | 0.017 | 0.106 | 623.5% |
| Pulmonary cancer 3 | 0.021 | 0.165 | 785.7% |
| Pulmonary cancer 4 | 0.033 | 0.149 | 451.5% |
| Pulmonary cancer 5 | 0.020 | 0.054 | 270.0% |
| Pulmonary cancer 6 | 0.043 | 0.280 | 651.2% |
| Pulmonary cancer 7 | 0.033 | 0.263 | 797.0% |
| Pulmonary cancer 8 | 0.041 | 0.252 | 614.6% |
| Pulmonary cancer 9 | 0.043 | 0.414 | 962.8% |
| Pulmonary cancer 10 | 0.038 | 0.167 | 439.5% |
| Pulmonary cancer 11 | 0.049 | 0.423 | 863.3% |
| Pulmonary cancer 12 | 0.037 | 0.213 | 575.7% |
| Pulmonary cancer 13 | 0.030 | 0.311 | 1036.7% |
| Pulmonary cancer 14 | 0.045 | 0.240 | 533.3% |
| Pulmonary cancer 15 | 0.037 | 0.222 | 600.0% |
| Pulmonary cancer 16 | 0.057 | 0.480 | 842.1% |
| Pulmonary cancer 17 | 0.043 | 0.212 | 493.0% |
| Pulmonary cancer 18 | 0.029 | 0.279 | 962.1% |
| Pulmonary cancer 19 | 0.076 | 0.484 | 636.8% |
| Pulmonary cancer 20 | 0.061 | 0.392 | 642.6% |
| SiSo cell supernatant | 1.573 | 1.928 | 122.6% |
| MBL 81 | 0.021 | 0.064 | 304.8% |
| MBL 82 | 0.014 | 0.124 | 885.7% |
| MBL 83 | 0.019 | 0.173 | 910.5% |
| MBL 84 | 0.018 | 0.188 | 1044.4% |
| MBL 85 | 0.013 | 0.193 | 1484.6% |
| MBL 87 | 0.013 | 0.162 | 1246.2% |
| MBL 86 | 0.562 | 0.598 | 106.4% |

| U/mL | | | |
|---|---|---|---|
| Specimen | No sialidase treatment | Sialidase treatment | Treatment/ No treatment |
| Pulmonary cancer 1-1 | 1.5 | 139.6 | 9561.6% |
| Pulmonary cancer 1-5 | 12.3 | 400.0 | 3241.5% |
| Pulmonary cancer 1-9 | 112.2 | 400.0 | 356.5% |
| Ovarian cancer 2-4 | 18.3 | 181.4 | 993.9% |
| Ovarian cancer 2-2 | 0.0 | 6.3 | ∞ |
| Ovarian cancer 2-7 | 7.8 | 400.0 | 5115.1% |
| Colonic cancer 3-10 | 1.4 | 92.9 | 6685.6% |
| Colonic cancer 3-6 | 1.0 | 324.1 | 32414.0% |
| Colonic cancer 3-5 | 4.3 | 400.0 | 9411.8% |
| Colonic cancer 3-9 | 7.4 | 400.0 | 5376.3% |
| Colonic cancer 3-4 | 5.8 | 400.0 | 6920.4% |
| Breast cancer 5-1 | 0.8 | 55.9 | 6813.4% |
| Pulmonary cancer 1 | 0.0 | 8.9 | ∞ |
| Pulmonary cancer 2 | 0.4 | 6.4 | 1820.0% |
| Pulmonary cancer 3 | 0.6 | 10.5 | 1847.4% |
| Pulmonary cancer 4 | 1.4 | 9.4 | 673.4% |
| Pulmonary cancer 5 | 0.5 | 2.9 | 572.0% |
| Pulmonary cancer 6 | 2.1 | 19.1 | 905.7% |
| Pulmonary cancer 7 | 1.4 | 17.8 | 1252.1% |
| Pulmonary cancer 8 | 2.0 | 16.9 | 855.1% |
| Pulmonary cancer 9 | 2.1 | 30.4 | 1460.6% |
| Pulmonary cancer 10 | 1.8 | 10.7 | 602.8% |
| Pulmonary cancer 11 | 2.5 | 31.1 | 1235.7% |
| Pulmonary cancer 12 | 1.7 | 14.0 | 822.9% |
| Pulmonary cancer 13 | 1.2 | 21.6 | 1828.8% |
| Pulmonary cancer 14 | 2.2 | 16.1 | 723.0% |
| Pulmonary cancer 15 | 1.7 | 14.7 | 862.4% |
| Pulmonary cancer 16 | 3.1 | 36.5 | 1187.9% |
| Pulmonary cancer 17 | 2.1 | 14.0 | 661.1% |
| Pulmonary cancer 18 | 1.1 | 19.0 | 1714.4% |
| Pulmonary cancer 19 | 4.4 | 36.9 | 847.1% |
| Pulmonary cancer 20 | 3.3 | 28.5 | 852.4% |
| SiSo cell supernatant | 243.3 | 400.0 | 164.4% |
| MBL 81 | 0.6 | 3.5 | 621.1% |
| MBL 82 | 0.0 | 7.6 | ∞ |
| MBL 83 | 0.4 | 11.1 | 2921.1% |
| MBL 84 | 0.5 | 12.2 | 2430.0% |
| MBL 85 | 0.0 | 12.5 | ∞ |
| MBL 87 | 0.0 | 100.3 | ∞ |
| MBL 86 | 44.8 | 49.0 | 109.4% |

400 U/mL or larger were all expressed as 400.0 U/mL.

| Specimen | Stage | No sialidase treatment | Sialidase treatment |
|---|---|---|---|
| Pulmonary cancer 1 | 1 | 0.0 | 8.9 |
| Pulmonary cancer 2 | 1 | 0.4 | 6.4 |
| Pulmonary cancer 3 | 1 | 0.6 | 10.5 |
| Pulmonary cancer 4 | 1 | 1.4 | 9.4 |
| Pulmonary cancer 5 | 1 | 0.5 | 2.9 |
| Pulmonary cancer 6 | 2 | 2.1 | 19.1 |
| Pulmonary cancer 7 | 2 | 1.4 | 17.8 |
| Pulmonary cancer 8 | 2 | 2.0 | 16.9 |
| Pulmonary cancer 9 | 2 | 2.1 | 30.4 |
| Pulmonary cancer 10 | 2 | 1.8 | 10.7 |
| Pulmonary cancer 11 | 3 | 2.5 | 31.1 |
| Pulmonary cancer 12 | 3 | 1.7 | 14.0 |
| Pulmonary cancer 13 | 3 | 1.2 | 21.6 |
| Pulmonary cancer 14 | 3 | 2.2 | 16.1 |
| Pulmonary cancer 15 | 3 | 1.7 | 14.7 |
| Pulmonary cancer 16 | 4 | 3.1 | 36.5 |
| Pulmonary cancer 17 | 4 | 2.1 | 14.0 |
| Pulmonary cancer 18 | 4 | 1.1 | 19.0 |
| Pulmonary cancer 19 | 4 | 4.4 | 36.9 |
| Pulmonary cancer 20 | 4 | 3.3 | 28.5 |

FIG. 10

Measurement of sera of patients with various cancers by ELISA

| Diagnosis | Number of specimens | Serum RCAS1 (U/mL) | | | | | No.>15U/mL | Positive rate (%) |
|---|---|---|---|---|---|---|---|---|
| | | Average | SD value | Median | Minimum | Maximum | | |
| Dermal cancer | 20 | 29.9 | 9.2 | 32.0 | 10.3 | 44.3 | 19 | 95.0 |
| Ovarian cancer | 42 | 476.6 | 263.6 | 15.7 | 6.4 | 1426.0 | 27 | 64.3 |
| Pulmonary cancer | 25 | 6265.5 | 30925.1 | 24.7 | 6.5 | 154700.8 | 21 | 84.0 |
| Colonic cancer | 29 | 72.0 | 153.4 | 22.3 | 5.0 | 787.1 | 23 | 79.3 |
| Breast cancer | 29 | 24.6 | 13.1 | 23.8 | 6.2 | 66.1 | 21 | 75.9 |
| Prostate cancer | 20 | 18.6 | 6.8 | 16.7 | 9.7 | 32.0 | 12 | 60.0 |
| Endometrium cancer | 20 | 15.5 | 2.8 | 14.3 | 10.5 | 20.4 | 9 | 45.0 |
| Testis cancer | 20 | 17.1 | 6.4 | 15.2 | 9.9 | 28.5 | 11 | 55.0 |
| Renal cancer | 20 | 18.9 | 3.2 | 18.3 | 13.5 | 25.1 | 18 | 90.0 |

F I G. 1 3

| Diagnosis | No. of Patiens | Serum RCAS1 (U/mL) | | | |
|---|---|---|---|---|---|
| | | Mean | SD | Range | Median | No.>15U/mL (%) |
| Ductal adenocarcinoma | 20 | 25.1 | 9.4 | 6.4-40.4 | 24.0 | 17 (85.0) |
| Intraductal papillary adenoma | 6 | 25 | 18.4 | 7.0-57.2 | 17.3 | 5 (83.3) |
| Chronic pancreatitis | 10 | 11 | 2 | 7.6-14.5 | 11.5 | 0 (0) |
| Acute pancreatitis | 5 | 12 | 7.2 | 5.8-24.1 | 9.9 | 1 (20.0) |
| Autoimmune pancreatitis | 5 | 7.1 | 1.4 | 5.6-9.4 | 6.7 | 0 (0) |

FIG. 15

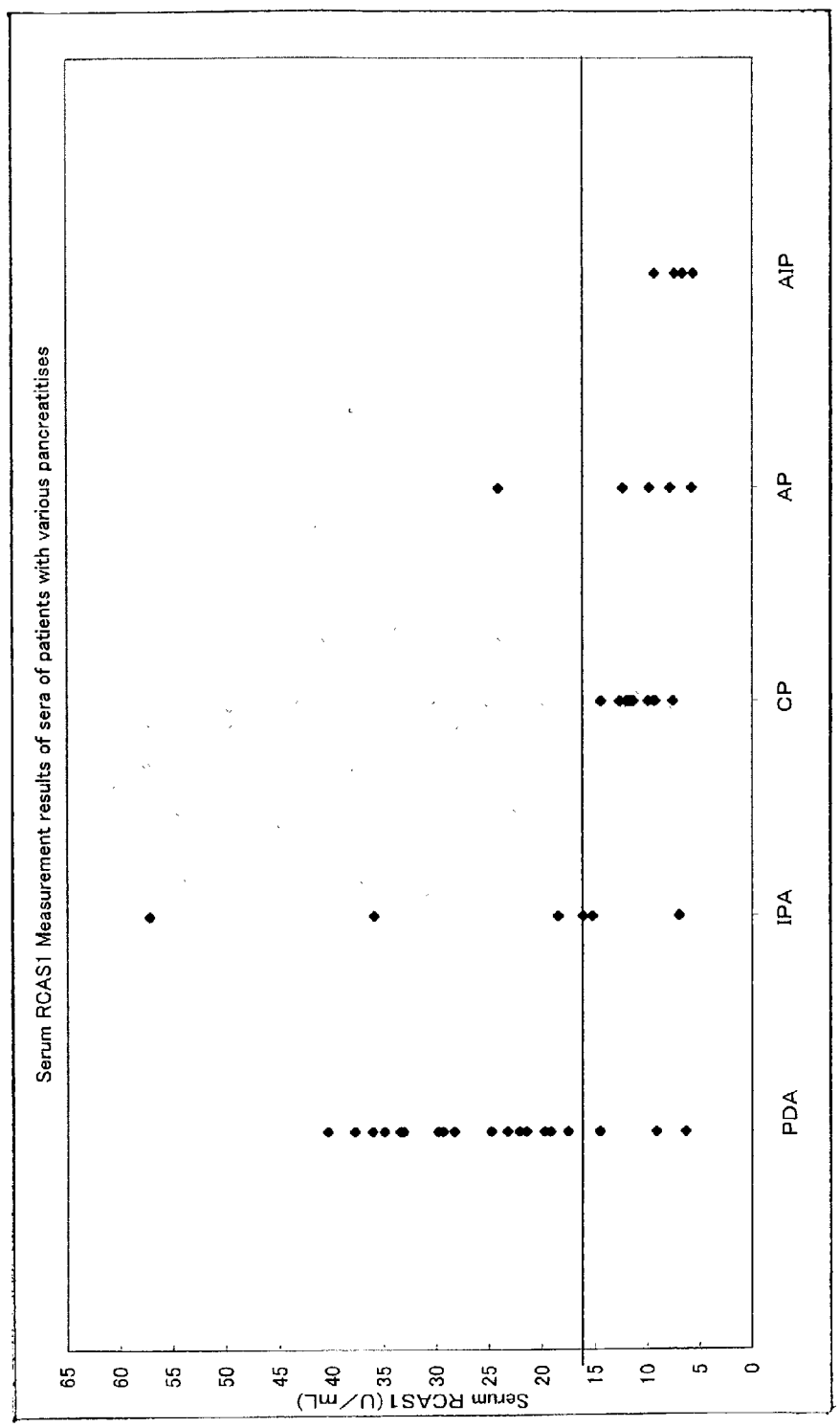
F I G. 16

| Diagnosis | No. of Patiens | Serum CA19-9 (U/mL) | | | | |
|---|---|---|---|---|---|---|
| | | Mean | SD | Range | Median | No.>35U/mL (%) |
| Ductal adenocarcinoma | 20 | 668 | 360 | 102-1212 | 687 | 20 (100) |
| Intraductal papillary adenoma | 6 | 170 | 88 | 90-303 | 142 | 6 (100) |
| Chronic pancreatitis | 10 | 76 | 14 | 50-92 | 78 | 10 (100) |
| Acute pancreatitis | 5 | 57 | 14 | 41-70 | 58 | 5 (100) |
| Autoimmune pancreatitis | 5 | 38 | 19 | 17-68 | 35 | 2 (40) |

Added up from measured values described in data sheet attached to purchased specimens

F I G. 1 7

|  | Sensitivity | Specificity | Accuracy |
|---|---|---|---|
| Serum RCAS1 | 85% | 95% | 89% |
| Serum CA19-9 | 100% | 15% | 63% |

FIG. 18

METHOD FOR IMMUNOLOGICALLY MEASURING RCAS1 AND KIT FOR MEASURING THE SAME

CROSS REFERENCES TO RELATED APPLICATION

This application is a continuation-in-part of now abandoned U.S. patent application Ser. No. 09/627,137 filed on Jul. 27, 2000 before Examiner Natalie A. Davis in Group Art Unit 1642, which is based upon priority of Japanese Patent Application No. 2000-22706 filed Jan. 31, 2000.

BACKGROUND OF THE INVENTION

The present invention relates to a method for immunologically measuring tumor-related antigen RCAS1 and kit for measuring the same, a method for immunologically measuring anti-RCAS1 antibody and a kit for measuring the same, and a method for immunologically measuring RCAS1 receptor.

In the study of human tumors, there have been reported some tumor-related antigens such as CEA, CA19-9, α-fetoprotein and the like. In addition, monoclonal antibodies against these tumor-related antigens have been made and it has been showed that the detection of tumor-related antigens using these monoclonal antigens is effective for diagnosis of cancer. Further, as an application to the cancer treatment, there has been studied a method for specifically binding an anti-cancer agent or a radioactive substance to these monoclonal antibodies and, thereby, cancer cells are specifically attacked.

However, expression of the above tumor-related antigen is not uniform depending upon tissues and, in a sense that cancers are widely detected, it cannot be said that a method for treatment or a method for diagnosis utilizing the above monoclonal antibody against the tumor-related antigen is sufficient. Thus, there is desired the study of novel tumor-related antigens and antibodies against them.

Further, there are many kinds of cancers, for example, malignant cancers having the strong infiltrating property, cancers having relatively better prognosis, cancers having the high sensitivity to chemical therapy and the like. It is desired that a method for diagnosis and a method for treatment are provided depending upon the nature of these cancers. In particular, determination whether prognosis is better or not has the important meaning in the treatment of cancers.

On the other hand, uterine neck adenocarcinoma which occupies 5 to 20% of adenocarcinomas has been studied. Such the cancer is known to have the lower sensitivity to radiation therapy and chemical therapy as compared with uterine neck platycyte cancer. The development of a method of treating that cancer is of course desired and the study of biological property of the adenocarcinoma and the sensitivity to radiation and the like is considered to be highly valuable also in the development of anti-cancer agents and a method for diagnosis in the other cancers.

In order to examine the biological property of uterine neck adenocarcinoma and the sensitivity to anti-cancer agents, the present inventors established the SiSo cell strain and reported the properties thereof (International Journal of Oncology 6: 1099–1104, 1995 and Cancer vol. 77 1501–1509, 1996). In the study thereafter, a monoclonal antibody (22-1-1 monoclonal antibody) against the SiSo cell was made and, by utilizing this, distribution in the tissues and the biological property of an antigen which is recognized by 22-1-1 monoclonal antibody were studied. As a result, it was revealed that the antigen which is recognized by 22-1-1 monoclonal antibody is strongly expressed in uterine cancer and ovary cancer, particularly infiltrating cancer (Cancer vol. 77 1501–1509, 1996).

The present inventors revealed an antigen (RCAS1) on the cancer cell which is recognized by 22-1-1 monoclonal antibody and at the same time studied its properties. As a result, it was found that RCAS1 functions as a ligand for a receptor of immunological cells (T cell, B cell, NK cell and the like) and the possibility was suggested that RCAS1 may play an important role upon development by escaping the immunological surveillance mechanism, by inhibiting growth of immunological cells and inducing cell death due to apoptosis. In addition, the possibility that RCAS1 or anti-RCAS1 antibody is involved in immunological diseases, for example, autoimmune disease can be also considered.

As described above, RCAS1 or anti-RCAS1 antibody is an useful subject for the diagnosis of cancers and autoimmune diseases as well as the study of development and infiltration of tumors and it is considered that they are important for studying the mechanism of apoptosis. That is, since it is considered that measurement of RCAS1 and the like is effective for detecting cancers and presuming prognosis and establishing therapeutic strategy on diseases and contributes to the study of apoptosis, the development of simple and high accuracy method for quantitating RCAS1 and the like is desired. In addition, simple and high accuracy measurement of an expressed amount of RCAS1 receptor in immunological cells can be an useful means for clarifying the mechanism by which cancer cells escape immunological surveillance mechanism.

BRIEF SUMMARY OF THE INVENTION

The present invention was done in view of the above problems and based on the above findings and provides a simple method for measuring RCAS1 which is a tumor-related antigen and a kit for measuring the same. The present invention also provides a simple method for measuring anti-RCAS1 antibody against RCAS1 and a kit for measuring the same. Further, the present invention provides a simple method for measuring RCAS1 receptor.

The present invention is a method for immunologically measuring RCAS1, which comprises a) a step of reacting a specimen with a first anti-RCAS1 antibody capable of specifically binding to RCAS1, b) a step of labeling the first reaction product produced by the above a) step, and c) a step of measuring a labeled amount of the labeled first reaction product.

According to such the method, the highly sensitive measurement of RCAS1 can be performed due to the high specificity of the first anti-RCAS1 antibody.

RCAS1 as used herein is an antigen which is recognized by an antibody (22-1-1 antibody) against the SiSo cell as described above. Our study showed that RCAS1 is a protein having a molecular weight of 78 kDa as determined by SDS-PAGE (Cancer vol. 77 1501–1509, 1996).

The present invention can further comprise the following steps: that is d) a step of reacting the above first anti-RCAS1 antibody with second RCAS1 as a standard substance, e) a step of labeling the second reaction product produced by the above d) step, f) a step of producing a calibration curve by measuring a labeled amount of the labeled second reaction product, and g) a step of quantitating RCAS1 in the specimen from a labeled amount of the first reaction product and the calibration curve.

In such the steps, a calibration curve is produced using second RCAS1 as a standard substance. A labeled amount of the first reaction product is quantitated based on the calibration curve, that is, RCAS1 in the specimen is quantitated.

Included in the present invention is a method for immunologically measuring RCAS1, which comprises the following essential features. It is a method for immunologically measuring RCAS1, which comprises a step of reacting a specimen with a solid phased RCAS1 antibody obtained by binding to an insoluble support a first anti-RCAS1 antibody capable of specifically binding to RCAS1 and, thereafter, reacting with a second anti-RCAS1 antibody labeled with a labeling substance and measuring a labeled amount of the produced first reaction product, a step of producing a calibration curve by reacting second RCAS1 as a standard substance with the solid phased RCAS1 antibody and measuring a labeled amount of the produced second reaction product, and a step of quantitating RCAS1 in the specimen from a labeled amount of the first reaction product and the calibration curve.

As the first anti-RCAS1 antibody, a solid phased anitbody bound to an insoluble support can be used and, in this case, the labeling can be performed by reacting a first reaction product or a second reaction product with a second anti-RCAS1 antibody labeled with a standard substance. That is, the labeling is performed by, after binding the first anti-RCAS1 antibody which has been solid phased in advance with RCAS1, and binding the second anti-RCAS1 labeled with a standard substance to the bound materials.

An example of an insoluble support used in a solid phased antibody is not limited to but includes a resin such as polystyrene resin, polycarbonate resin, silocone resin, nylon resin and the like, and a water-insoluble material such as glass and the like. Binding of the first anti-RCAS1 antibody onto this insoluble support is performed by physical adsorption or chemical adsorption.

A second anti-RCAS1 antibody is an antibody which recognizes a site of RCAS1 differing from a site recognized by the first anti-RCAS1 antigen and specifically binds to RCAS1.

Provided that, when RCAS1 in a specimen forms a polymer, an antibody which recognizes the same site as that recognized by the first anti-RCAS1 antibody can be used as a second anti-RCAS1 antibody. For example, the same antibody as the first anti-RCAS1 antibody may be used as a second anti-RCAS1 antibody.

As the first anti-RCAS1 antibody, a monoclonal antibody which recognizes RCAS1 is suitably used. As a result, high accuracy measurement becomes possible due to high specificity of a monoclonal antibody. For example, a monoclonal antibody produced by a hybridoma which is deposited at the Ministry of International Trade and Industry, National Institute of Bioscience and Human-Technology, Agency of Industrial Science and Technology which is an international depository authority under accession number FERM BP-7002 is used.

As a second RCAS1, RCAS1 derived from the SiSo cell is used. Alternatively, recombinant RCAS1 (hereinafter referred to as "rRCAS1") can be used. rRCAS1 is preferable in that it can be produced at a large amount and homogeneously. As an rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used.

As a labeling substance, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a specimen, living body fluid such as serum, plasma, urine, cerebrospinal fluid, ascites, thoracic fluid and the like can be used. Preferably, serum is used. When serum is used, simple measurement is possible.

In the other aspect of the present invention, RCAS1 can be measured by the following method. That is, it is a method for immunological measurement, which comprises a) a step of competely reacting an anti-RCAS1 antibody capable of specifically binding to RCAS1, with a specimen and RCAS1 which was labeled in advance, and b) a step of measuring a labeled amount of the reaction product produced by the a) step.

In such a method, by measuring an amount of labeled RCAS1 bound to anti-RCAS1 antibody, an amount of RCAS1 in the specimen is indirectly measured. Here, an amount of RCAS1, which was labeled in advance, for competitively reacting with each specimen is constant. Thereby, when an amount of RCAS1 in the specimen is large, an amount of labeled RCAS1 which binds to an anti-RCAS1 antibody is relatively decreased. To the contrary, when an amount of RCAS1 in the specimen is small, an amount of labeled RCAS1 which binds to an anti-RCAS1 antibody is relatively increased. Thus, an amount of RCAS1 in the specimen is calculated from an amount of labeled RCAS1 bound to an anti-RCAS1 antibody.

In the aforementioned method, an anti-RCAS1 antibody is preferably used by binding to an insoluble support. An example of an insoluble support is not limited to but includes a resin such as polystyrene resin, polycarbonate resin, silicone resin, nylon resin and the like, and a water-insoluble substance such as glass and the like. Binding of the anti-RCAS1 antibody onto this insoluble support is performed by physical adsorption or chemical adsorption.

As an anti-RCAS1 antibody, a monoclonal antibody which recognizes RCAS1 is suitably used. As a result, high accuracy measurement becomes possible due to high specificity of a monoclonal antibody. For example, a monoclonal antibody produced by a hybridoma which is deposited at the Ministry of International Trade and Industry, National Institute of Bioscience and Human-Technology, Agency of Industrial Science and Technology which is an international depository authority under accession number FERM BP-7002 is used.

As RCAS1 which was labeled in advance, RCAS1 derived from the SiSo cell is used. Alternatively, rRCAS1 can be used. rRCAS1 is preferable in that it can be produced at a large amount and homogeneously. As rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used.

For labeling RCAS1, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a specimen, living body fluid such as serum, plasma, urine, cerebrospinal fluid, ascites, thoracic fluid and the like can be used. Preferably, serum is used. When serum is used, simple measurement is possible.

In the above methods, a specimen can be subjected to the sialidase treatment before an antigen-antibody reaction between a specimen and an anti-RCAS1 antibody is performed. That is, the first aspect of the present invention also provides the following method: a method for immunologically measuring RCAS1, which comprises A) a step of treating a specimen with sialidase, and B) a step of measuring RCAS1 contained in a specimen after the sialidase treatment, by utilizing an antigen-antibody reaction between RCAS1 and an first anti-RCAS1 antibody.

In step A), a specimen is treated with sialidase. As the sialidase, the known sialidases can be used. For example, commercially available Arthrobacter ureafaciens-derived sialidase (manufactured by Sigma) can be used. The conditions for sialidase reaction are not particularly limited as long as the conditions are such that added sialidase can effectively act, and can be appropriately set by taking into consideration a kind of sialidase to be used, a kind of a specimen to be subjected to measurement and the like. For example, when serum is used as a specimen, there are the reaction conditions under which a specimen is diluted with a suitable buffering solution such as acetate buffer and the like, and sialidase is added to the final concentration of 0.5 mU/ml-4 mU/ml, preferably about 1 mU/ml, followed by a reaction at about 37° C. for 1 hour.

In this respect, it is expected that conformation of RCAS1 in a specimen is changed by the sialidase treatment and, as a result, the binding property of the RCAS1 to an anti-RCAS1 antibody varies.

A specimen after the sialidase treatment is subjected to an antigen-antibody reaction using a first anti-RCAS1 antibody. As the antigen-antibody reaction, any of a method for competitively reacting RCAS1 in a specimen and separately prepared RCAS1 for the first anti-RCAS1 antibody (competitive method), and a method for reacting non-competitively (that is, a method for reacting only RCAS1 in a specimen: non-competitive method).

One example of the former is a method for B1) reacting competitively a specimen after the sialidase treatment and labeled RCAS1 for the first anti-RCAS1 antibody, and B2) measuring an amount of a label bound to the first anti-RCAS1 antibody. In such the method, an amount of RCAS1 in a specimen is indirectly measured by measuring an amount of labeled RCAS1 bound to the first anti-RCAS1 antibody. That is, when an amount of RCAS1 in a specimen is large, an amount of labeled RCAS1 to be bound to the first anti-RCAS1 antibody is relatively decreased. Conversely, when an amount of RCAS1 in a specimen is small, an amount of labeled RCAS1 to be bound to the first anti-RCAS1 antibody is relatively increased, whereby, an amount of RCAS1 in a specimen is obtained from this increase and decrease. Herein, it is preferable that the first anti-RCAS1 antibody is a solid-phased antibody bound to an insoluble support from a viewpoint of easy operation and detection sensitivity.

In addition to the aforementioned method, measurement utilizing a competitive antigen-antibody reaction is also possible by the following method: That is, it is a method for B3) competitively reacting a specimen after the sialidase treatment and the labeled first anti-RCAS1 antibody for RCAS1, and B4) measuring an amount of the label bound to RCAS1. In addition, it is a method for B5) competitively reacting a specimen after the sialidase treatment and the first anti-RCAS1 antibody for RCAS1, B6) labeling the first anti-RCAS1 antibody bound to RCAS1 and, finally, B7) measuring an amount of the label bound to RCAS1 via the first anti-RCAS1 antibody. The labeling of the first anti-RCAS1 antibody can be performed by using a labeled antibody (secondary antibody) to the first anti-RCAS1 antibody.

Also in these methods, an amount of RCAS1 in a specimen is obtained by measuring an amount of a label directly or indirectly bound to RCAS1. Herein, it is preferable that RCAS1 to be competitively reacted with a specimen is a solid-phased RCAS1 bound to an insoluble support from a viewpoint of easy operation and detection sensitivity.

Next, one example of a non-competitive method is shown. That is, it is a method for reacting a specimen after the sialidase treatment and the first anti-RCAS1 antibody, labeling the resulting antigen-antibody reaction product and measuring an amount of the label. In this method, an amount of the antigen-antibody reaction product in which RCAS1 in a specimen is bound to the first anti-RCAS1 antibody, is directly measured as an amount of a label. Herein, labeling of the antigen-antibody reaction product can be performed by binding to the antigen-antibody reaction product a labeled antibody obtained by labeling the second anti-RCAS1 antibody. Alternatively, labeling can be performed by binding the second anti-RCAS1 antibody to the antigen-antibody reaction product and binding a labeled antibody (secondary antibody) to the second anti-RCAS1 antibody.

In this respect, also in a non-competitive method, it is preferable that the first anti-RCAS1 antibody is a solid-phased antibody bound to an insoluble support from a viewpoint of measurement sensitivity and easy operation.

The second aspect of the present invention is a kit for immunologically measuring RCAS1, which comprises a solid phased antibody obtained by binding to an insoluble support a first anti-RCAS1 antibody capable of specifically binding to RCAS1, a second anti-RCAS1 antibody capable of specifically binding to RCAS1 labeled with a labeling substance, and RCAS1 as a standard substance.

As the first anti-RCAS1 antibody in the second aspect of present invention, a monoclonal antibody which recognizes RCAS1 is suitably used. As a result, high accuracy measurement becomes possible due to high specificity of a monoclonal antibody. For example, a monoclonal antibody produced by a hybridoma which is deposited at the Ministry of International Trade and Industry, National Institute of Bioscience and Human-Technology, Agency of Industrial Science and Technology which is an international depository authority under accession number FERM BP-7002 is used.

An example of an insoluble support is not limited to but includes a resin such as polystyren resin, polycarbonate resin, silicone resin, nylon resin and the like, and a water-insoluble substance such as glass and the like. Binding of the first anti-RCAS1 antibody onto this insoluble support is performed by physical adsorption or chemical adsorption.

A second anti-RCAS1 antibody is an antibody which recognizes a site of RCAS1 differing from a site recognized by the first anti-RCAS1 and specifically binds to RCAS1.

As a labeling substance, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a standard substance RCAS1, RCAS1 derived from the SiSo cell is used. Alternatively, rRCAS1 can be used. rRCAS1 is preferable in that it can be produced at a large amount and homogeneously. As rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used.

By adding sialidase to the aforementioned kit, a kit can be constructed by which an amount of RCAS1 in a specimen can be measured by conducting the sialidase treatment of a specimen and an antigen-antibody reaction between RCAS1 and an anti-RCAS1 antibody. That is, as a kit for utilizing a non-competitive method, there are provided (1) a kit for immunologically measuring RCAS1, which comprises sialidase, a solid-phased first anti-RCAS1 antibody, and a labeled second anti-RCAS1 antibody, and (2) a kit for immunologically measuring RCAS1, which comprises sialidase, a solid-phased first anti-RCAS1 antibody, a second anti-RCAS1 antibody, and a labeled antibody specifically binding to the aforementioned second anti-RCAS1 antibody, On the other hand, as a kit for utilizing a competitive method, there are provided (1) a kit for immunologically measuring RCAS1, which comprises sialidase, a solid-phased first anti-RCAS1 antibody, and the labeled first RCAS1, (2) a kit for immunologically measuring RCAS1, which comprises sialidase, the solid-phased first RCAS1, and a labeled first anti-RCAS1 antibody, and (3) a kit for immunologically measuring RCAS1, which comprises the solid-phased first RCAS1, a first RCAS1 antibody, and a labeled antibody to the first RCAS1 antibody.

In the above kits, it is preferable that the first anti-RCAS1 antibody is a monoclonal antibody in order to perform measurement with the high detection sensitivity. For example, as the first anti-RCAS1 antibody, a monoclonal antibody produced by hybridoma of accession number FERM BP-7002 can be used.

Herein, a kit for immunologically measuring RCAS1 can be constructed by further inclusion of RCAS1 as a standard (standard RCAS1). The standard RCAS1 can be utilized for producing a calibration line and, thus, a kit is obtained which can easily quantitate an amount of RCAS1 in a specimen. The aforementioned kits may contain a reagent for sialidase reaction (such as buffering solution), and a reagent for an antigen-antibody reaction (such as buffering solution, chromogenic substrate, chromogenic reagent, color developing reaction, stopping solution and the like).

A kind of usable sialidase, a method for solid-phasing a second anti-RCAS1 antibody, a first anti-RCAS1 antibody and the like, a method for labeling the first RCAS1 and the like, and the like are the same as those in the first aspect of the present invention.

The third aspect of the present invention is a method for immunologically measuring an anti-RCAS1 antibody, which comprises 1) a step of reacting RCAS1 with a specimen, 2) a labeling step of reacting the first reaction product produced by the 1) step with an anti-human immunoglobulin antibody labeled with a labeling substance, and 3) a step of measuring a labeled amount of the labeled first reaction product.

The third aspect of the present invention can further comprises the following steps: that is 4) a step of reacting the RCAS1 with a standard specimen, 5) a step of labeling by reacting the second reaction product produced by the 4) step with an anti-human immunoglobulin antibody labeled with the labeling substance, 6) a step of producing a calibration curve by measuring a labeled amount of the labeled second reaction product, and 7) a step of quantitating an anti-RCAS1 antibody in the specimen from a labeled amount of the first reaction product and the calibration curve.

In such the steps, a calibration curve is produced using a standard specimen. A labeled amount of the first reaction product is quantitated based on the calibration curve, that is, an anti-RCAS1 antibody in the specimen is quantitated.

RCAS1 can be used by binding to an insoluble support. An example of an insoluble support for rendering it into solid phase is not limited to but includes a resin such as polystyrene resin, polycarbonate resin, silicone resin, nylon resin and the like, and a water-insoluble substance such as glass and the like. Binding of the first anti-RCAS1 antibody onto this insoluble support is performed by physical adsorption or chemical adsorption.

As RCAS1, RCAS1 derived from the SiSo cell can be used. Alternatively, rRCAS1 can be used. rRCAS1 is preferable in that it can be produced at a large amount and homogeneously. As rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used.

As an anti-human immunoglobulin antibody, an antibody which recognizes each class of a human immunoglobulin such as IgG, IgM and the like can be used. An anti-human immunoglobulin which can recognize a plurality of classes of an immunoglobulin can be used. Alternatively, a combination of immunoglobulins which recognizes the particular class may be used. Further, an anti-human immunoglobulin antibody which recognizes only the particular class of an immunoglobulin can be used. In this case, this class of anti-RCAS1 antibody can be specifically detected and quantitated.

An anti-human immunoglobulin antibody is used by labeling with a labeling substance. Labeling can be conducted by the well-known method and the commercially available labeled anti-human immunoglobulin antibody may be utilized.

As a labeling substance, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a specimen, living body fluid such as serum, plasma, urine, cerebrospinal fluid, ascites, thoracic fluid and the like can be used. Preferably, serum is used. When serum is used, simple measurement is possible.

As a standard specimen, an anti-RCAS1 antibody-positive specimen is used. For example, when serum is used as a specimen, anti-RCAS1 antibody-positive serum is used.

The fourth aspect of the present invention is a kit for immunologically measuring an anti-RCAS1 antibody, which comprises solid phased RCAS1 obtained by binding RCAS1 to an insoluble support, an anti-human immunoglobulin antibody labeled with a labeling substance, and a standard specimen.

An example of an insoluble support used for rendering RCAS1 into solid phase in the fourth aspect of the present invention is not limited to but includes a resin such as polystyrene resin, polycarbonate resin, silicone resin, nylon resin and the like, and a water-insoluble substance such as glass and the like. Binding of a RCAS1 antibody onto this insoluble support is performed by physical adsorption or chemical adsorption.

As RCAS1, RCAS1 derived from the SiSo cell can be used. Alternatively, rRCAS1 can be used. rRCAS1 is preferable in that it can be produced at a large amount and homogeneously. As rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used.

As an anti-human immunoglobulin antibody, an antibody which recognizes each class of a human immunoglobulin such as IgG, IgM and the like can be used. An anti-human immunoglobulin which can recognize a plurality of classes of an immunoglobulin can be used. Alternatively, a combination of immunoglobulins which recognize the particular class may be used. Further, an anti-human immunoglobulin antibody which recognizes only the particular class of immunoglobulin can be used. In this case, this class of anti-RCAS1 antibody can be specifically detected and quantitated.

An anti-human immunoglobulin antibody is used by labeling with a labeling substance. Labeling can be conducted by the well-known method and the commercially available labeled anti-human immunoglobulin antibody may be utilized.

As a labeling substance, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a standard specimen, an anti-RCAS1 antibody-positive specimen can be used. For example, an anti-RCAS1 antibody-positive living body fluid such as serum, plasma, urine, cerebrospinal fluid, ascites, thoracic fluid and the like are used.

The fifth aspect of the present invention is a method for immunologically measuring a RCAS1 receptor in a specimen, which comprises I) a step of reacting an anti-RCAS1 antibody capable of specifically binding to first RCAS1 and second RCAS1 labeled with a labeling substance after the first RCAS1 is added to a specimen to incubate, and II) a step of measuring a labeled amount of the second RCAS1 bound to the anti-RCAS1 antibody.

As an anti-RCAS1 antibody in the fifth aspect of the present invention, a monoclonal antibody which recognizes RCAS1 is suitably used. As a result, high accuracy measurement becomes possible due to high specificity of a monoclonal antibody. For example, a monoclonal antibody produced by a hybridoma which is deposited at the Ministry of International Trade and Industry, National Institute of Bioscience and Human-Technology, Agency of Industrial Science and Technology which is an international depository authority under accession number FERM BP-7002 is used.

As first RCAS1 and second RCAS1, RCAS1 derived from the SiSo cell can be used. Alternatively, rRCAS1 can be used. rRCAS1 is preferable in that it can be produced at a large amount and homogeneously. As rRCAS1, rRCAS1-GST (glutathione-5-transferase) fusion protein is suitably used. That is, RCAS1 which is expressed as a fusion protein with GST is used. Such the rRCAS1 can be simply purified by the conventional method. In addition, in place of GST, β-galactosidase, maltose-bound protein, histidine (His) tag and the like can be used. The first RCAS1 and the second RCAS1 may be same or different.

As a labeling substance, a member arbitrarily selected from peroxidase, β-D-galactosidase, microperoxidase, alkaline phosphatase, biotin and radioactive substance is suitably used. In particular, according to a method in which biotin is used as a labeling substance and avidin peroxidase is reacted, higher sensitive measurement can be performed. In the case where a radioactive substance is used, measurement can be performed by a RIA method.

As a specimen, living body fluid such as serum, plasma, urine, cerebrospinal fluid, ascites, thoracic fluid and the like are used. Preferably, serum is used. When serum is used, simple measurement possible.

According to the present invention, simple and high accuracy measurement of RCAS1 or anti-RCAS1 antibody in a specimen becomes possible. Thereby, means for detecting cancer or the like and presuming prognosis is provided, being useful. In addition, means for clarifying the mechanism of apoptosis is provided, being useful.

In particular, a method of subjecting an anti-RCAS1 antibody to an antigen-antibody reaction after treatment of a specimen with sialidase enables RCAS1 in a specimen to be measured at the high sensitivity. In addition, the correlation between clinical stage and a measured value of RCAS1 is perceived in some diseases and, thus, according to a method for measuring RCAS1 at the high sensitivity provided by the present invention, it becomes possible to diagnose more detailed symptom and monitor progress of symptom.

DETAILED DESCRIPTION OF THE DRAWINGS

These and other objects and technical advantages of the present invention will be readily apparent from the following description of the preferred exemplary embodiments of the invention in conjunction with the accompanying drawings, in which:

FIG. 1 is a graph showing the results from measurement of antibody titer of anti-serum in a process for producing an anti-RCAS1 polyclonal antibody.

FIG. 3 is a table showing the results of quantitaion of RCAS1 in each cancer patient.

FIG. 6 is a view showing a nucleotide sequence (SEQ ID NO: 1) of cDNA coding for RCAS1 and an amino acid sequence (SEQ ID NO: 2) for RCAS1.

FIG. 8 is a table summarizing the results of measurement of RCAS1 in serum of patients with various cancers using the ELISA method. The left column of FIG. 8 is a table summarizing a value of OD450/620 of each specimen, and the right column is a table summarizing the concentration (U/mL) calculated from a standard curve.

FIG. 10 is a table summarizing the results of measurement of RCAS1 in serum of patients with pulmonary cancers at the different clinical stage using the ELISA method.

FIG. 13 is a table summarizing the results of measurement of the RCAS1 concentration in sera of patients with various cancers (20 serum specimens of patients with dermal cancer, 42 serum specimens of patients with ovarian cancer, 25 serum specimens of patients with pulmonary cancer, 29 serum specimens of patients with colonic cancer, 29 serum specimens of patients with breast cancer, 20 serum specimens of patients with prostate cancer, 20 serum specimens of patients with endometrium cancer, 20 serum specimens of patients with testis, 20 serum specimens of patients with renal cancer).

Figure 14:
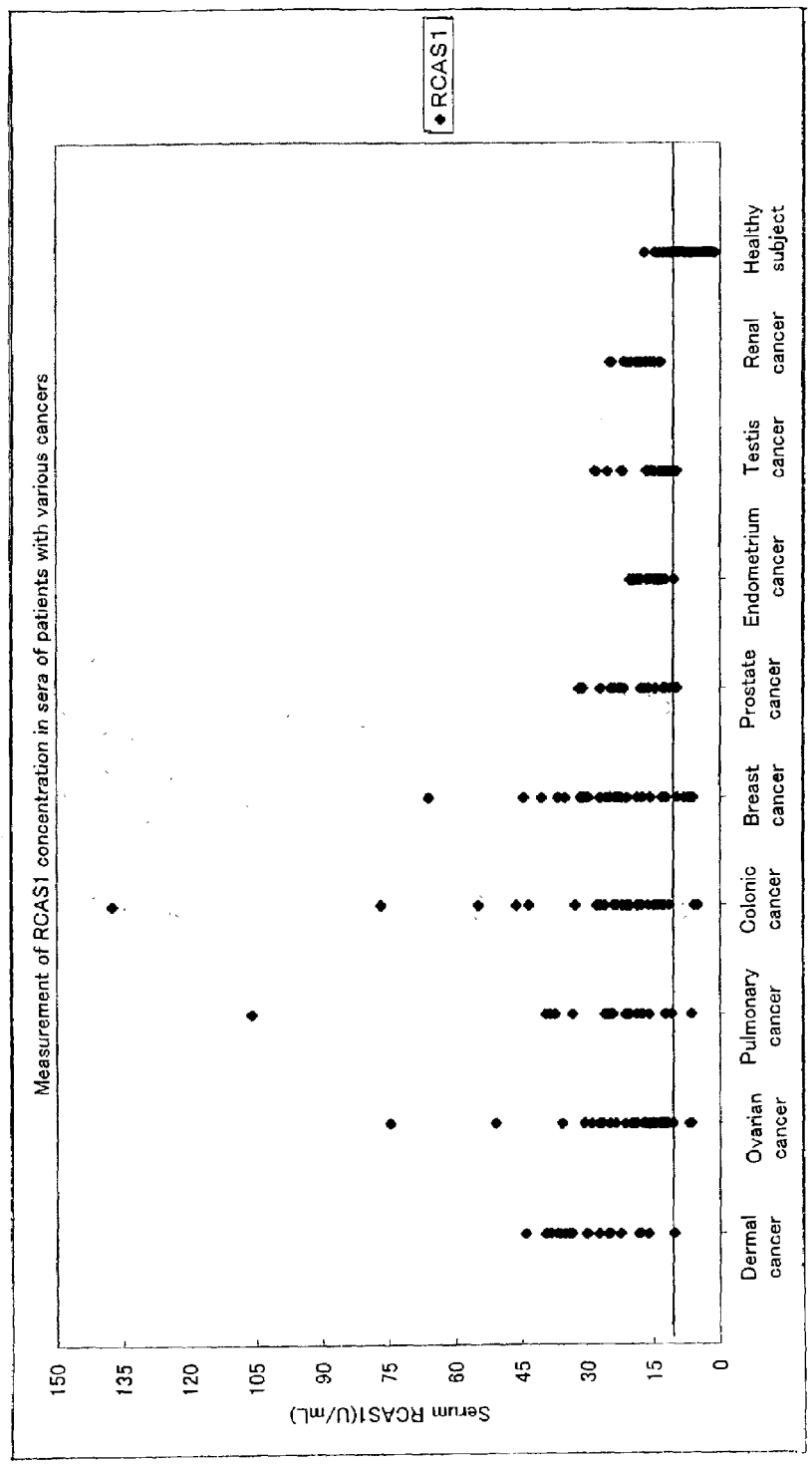

FIG. 14 illustrates graphically an amount of RCAS1 in sera of patients with various cancers, and the RCAS1 concentration of each specimen is plotted per a diagnosed name.

FIG. 15 is a table summarizing the results of measurement of the RCAS1 concentration in sera of patients with various pancreatic diseases, and Mean (average value), SD (standard deviation), Range (minimum and maximum), Median, number of positive specimens and positive rate are shown per a diagnosed name.

FIG. 16 is a graph in which the results of measurement of the RCAS1 concentration in sera of patients with pancreatic diseases are plotted.

FIG. 17 is a table summarizing Means (average value) of an amount of a tumor marker, CA19-9, in sera of patients with various pancreatic diseases, SD (standard deviation), Range (minimum and maximum), Median, number of positive specimens and positive rate.

FIG. 18 is a table comparing RCAS1 and CA19-9 for the sensitivity, the specificity and the accuracy.

DETAILED DESCRIPTION OF THE INVENTION

EXAMPLE 1

Production of Anti-RCAS1 Monoclonal Antibody

Production of anti-RCAS1 monoclonal antibody was performed according to a method which we reported in our previous paper (International Journal of Oncology 6: 1099–1104, 1995 and Cancer vol. 77 1501–1509, 1996). The method is shown below.

(1—1) Establishment of SiSo Cell Line Derived from Uterine Neck Cancer

Tumor tissue isolated from a Japanese woman, 67 years old, who was complaining of post-menopausal genital bleeding was cut into small pieces with scissors and stirred in Hanks Balanced salt solution (manufactured by GIBCO Life Technologies, Inc.) containing 0.25% trypsin and 0.02% EDTA for 30 minutes. After this was centrifuged, the precipitates were suspended in RPMI-1640 culture solution containing 20% FCS (manufactured by Whittaker Bioproduct), 100 unit/ml penicillin and 100 µg/ml streptomycin. The cells were cultured in a 25 mm$^2$ tissue culture flask at 37° C. in a humidified air of 5% $CO_2$ after the tumor cell colonies were observed, the culture solution was replaced with RPMI-1640 culture solution with 10% FCS added and subculturing was performed every 5 days.

Tumor cell grew very slowly in the primary culture and did not reach confluency. About 1 month later, the tumor cell colonies were detached from fibroblast by trypsinization and transferred to a new flask. The numbers of fibroblasts gradually decreased and disappeared from the tumor cell population in in-vitro. At this time point, tumor cells began to grow rapidly and were subcultured every 5 days. The tumor cell line was maintained for 36 months or longer after establishment and was termed as SiSo.

(1-2) Preparation of Antibody Producing Cells $1 \times 10^6$ SiSo cells were injected subcutaneously into Balb/c mouse (6 weeks age, female) together with 0.5 ml of a complete adjuvant. After 2 weeks, a mixture of $1 \times 10^6$ SiSo cells and incomplete Fruend adjuvant (manufactured by organon Technica) was injected intraperitoneally as a second immunization. $1 \times 10^6$ SiSo cells (1 ml in PBS (pH7)) sonicated was used as a booster immunization. 4 days after booster immunization, spleen cells were isolated. After the isolated spleen cells were mashed on a stainless mesh in a serum-free RPMI-1640 culturing solution, the spleen cell solution was centrifuged (1500 rpm, 7 minutes). The centrifugation residue was recovered and suspended in a serum-free RPMI-1640 culturing solution. Further, the suspension was washed with a serum-free RPMI-1640 culturing solution twice and mouse antibody producing spleen cells were obtained.

(1-3) Preparation of Mouse Myeloma Cells

As mouse myeloma cells, mouse myeloma cell strain X63.Ag8.653 was used. Mouse myeloma cells were cultured in RPMI-1640 complete medium (manufactured by Whittaker Bioproduct) with 10% v/v FCS containing L glutamine (1 mM, manufactured by Flow Laboratory), β-mercapto ethanol ($5 \times 10^{-6}$, manufactured by GIBCO Life Technologies, Inc.), N-2-hydoroxyethylpiperadine-N'-2-ethane-sulfonic acid (Hepes) (pH7.2) (10 mM, manufactured by GIBCO Life Technologies, Inc.), nonessential amino acid (0.1 mM, manufactured GIBCO Life Technologies, Inc.) and pyruvate sodium (1 mM, manufactured by GIBCO Life Technologies, Inc.).

(1-4) Preparation of Monoclonal Antibody Producing Hybridoma and Preparation of 22-1-1 Monoclonal Antibody (Anti-RCAS1 Monoclonal Antibody)

The antibody producing mouse spleen cells prepared as described above and the above mouse myeloma cells were fused (spleen cells: mouse myeloma cells=5:1) using polyethylene glycol 4000 to obtain a plurality of colonies of hybridoma.

In order to screen a hybridoma producing a monoclonal antibody against the SiSo cell, the culture supernatant of each hybridoma was taken and this was used to stain the SiSo cell by an indirect fluorescent antibody method. As a result, a hybridoma showing positive was subcloned by a limited diluting method to obtain a hybridoma clone.

The culture supernatant of the cloned hybridoma was screened by an indirect immunofluorescent method by utilizing the fact that it binds to uterine or ovary cancer but does not bind to other tumor cells. The resulting positive clone was designated 22-1-1. This hybridoma clone 22-1-1 was deposited at the international depositary authority as described below.

Depository Authority:
Name: The Ministry of International Trade and Industry, National Institute of Bioscienc and Human-Technology, Agency of Industrial Science and Technology
Address: 1-1-3 Higashi, Tsukuba-shi, Ibaragi-ken, Japan (ZIP 305-8566)
Accession number: FERM BP-7002
Deposit date: Jan. 20, 2000

A monoclonal antibody (22-1-1 monoclonal antibody) which the hybridoma clone produces was prepared from the culture supernatant of the hybridoma clone 22-1-1. The 22-1-1 monoclonal antibody was confirmed to be IgM class.

EXAMPLE 2

Preparation of Recombinant RCAS1 (rRCAS1-GST Fusion Protein) as a Standard Substance (2-1) cDNA Cloning and cDNA Analysis of RCAS1

The total RNA was extracted from the SiSo cell by the guanidium isothiocyanate-cesium chloride gradient method. The total RNA was purified using oligo dT column (manufactured by Pharmacia K. K.) to obtain poly(a)+RNA which was transcribed using a ZAP-cDNA synthesis kit (manufactured by Stratagene) to obtain a cDNA. Size-fractionated cDNA was inserted into the mammalian expression vector, pME-18SF(−), pyori-, ER- (supplied by H. Maruyama) in a sense orientation (EcoRI-XhoI) and was used to produce a cDNA library.

Subsequently, the trypsinized 293T cell ($5 \times 10^6$) were transformde with a mixture of the purified plasmid from the cDNA library and lypofectin (manufactured by Life Technologies, Inc.) for 5 hours at 37□ in serum-free DMEM. The cells were washed once and cultured in RPMI-1640 containing 10% FCS for 48 hours. The cells after culturing were trypsinized, the above 22-1-1 antibody was added to incubate on ice for 30 minutes. The sample after incubation was washed, followed by the reaction with secondary antibody. As the secondary antibody, FITC-labeled goat anti-mouse IgM was used.

5 μg/ml of propidium iodide was added thereto to stain the dead cell. The live cells expressing the antigen were separated with a flow cytometer and the plasmid DNA was extracted by a method of Hirt et al.

Thereafter, the base sequence of the end cDNA was examined from the extracted plasmid DNA using DyeDeoxy Terminator cycle Sequencing kit and 337-DNA Sequencer system.

As a result, it was found that the cDNA coding for RCAS1 contains a 5' untranslated region of 242 nucleotides, a coding region of 639 nucleotides (SEQ ID NO.:1) and 3' untranslated region of 179 nucleotides of. SEQ ID NO.:2 is an amino acid sequence (213 amino acids) coded by the cDNA. FIG. 6 shows the base sequence of cDNA coding RCAS1 and the amino acid sequence.

(2—2) Construction of rRCAS1-GST Fusion Protein

In order to produce rRCAS1-GST fusion protein, the full-length RCAS1 cDNA prepared in the (2-1) was digested with NotI and XhoI to make a blunt and, which was in-frame bound into SmaI site of procaryotic expression vector pGEX5x-1 (manufactured by Pharmacia K. K.). This expression vector was used to transform *Escherichia coli* BLR(DE3) pLysS, which was incubated with 0.1M isopropyl-β-D-thiogalactopyranoside for 3 hours to express in *Escherichia coli*. Thereafter, the *Escherichia coli* cell was sonicated in a cell lysis buffer (0.1 v/v % Triton X-100-containing 1×PBS). After intact cells and debris were removed by centrifugation, the GST fusion protein was purified using gluthatione-Sepharose beads (Pharmacia K. K.). In order to remove the remaining surfactant, the purified fusion protein was applied onto Ampure DT column (Amersham Medical Ltd.) and dialyzed against 1×PBS. The purified fusion protein was sterilized by passing it through a 0.2 μm filter, divided and frozen at −80° C.

EXAMPLE 3

Preparation of Anti-RCAS1 Polyclonal Antibody (3-1) Immunization and Obtaining of Anti-Serum Rabbit (Japanese white female, 3.5 kg) was immunized subcutaneously (about 10 places, 1/week) using the rRCAS1-GST fusion protein obtained in the (2—2) and, after the fifth immunization, a small amount of blood was taken from parotid vein, serum was separated and antibody titer was checked by ELISA method. That is, rRCAS1-GST fusion protein was dissolved in 1/100M phosphate buffered physiological sodium clolide solution (PBS) to prepare a 0.1 mg/ml solution, 10 μl of this solution was added to a 96-well microplate "Maxisoap" manufactured by Nunc, allowed to stand for 3 hours, the solution was removed by aspiration, 30 μl of PBS containing 5% bovine serum albumin was added to stand at 4° C. for about 18 hours, to block the unreacted part of the cup. After removal of the blocking solution and 3 times washing with 300 μl PBS, anti-serum series diluted with PBS was made, each 100 μl of these solution was added to each cup, allowed to stand for 1 hour to remove the reaction solution, followed by washing with 30 μl PBS 4 times. Then, 100 μl of the diluted peroxidase-labeled anti-rabbit IgG (manufactured by Medical and Biological Laboratories, Co., Ltd.) was added, allowed to stand to react at room temperature (20–25° C.) for 1 hour, which was washed again similarly, 100 μl of a solution of 3,3',5,5'-tetramethylbenzidine and hydrogen peroxide was added as a color developing substrate to react for a certain hour, 1.5M phosphoric acid was added to stop the reaction, and absorbance at the wavelength 450 nm was measured. The results of the measurement are shown by a graph of FIG. 1. As apparent from this FIG. 1, the resulting anti-serum shows the sufficient antibody titer. 70 ml of blood was taken from parotid vein of the rabbit showing such sufficient antibody titer to obtain about 30 ml of anti-serum.

(3-2) Purification of Anti-Serum

Since the reactivity to not only RCAS1 but also GST is induced when immunized with rRCAS1-GST, an antibody against GST is present in the anti-serum obtained in (3-1). In order to remove such the antibody (in order to remove or absorb the reactivity to GST), the anti-serum was first applied to rGST-bound Sepharose 4B Gel. Subsequently, the eluted fraction after washing with a sufficient amount of PBS was checked for the reactivity with GST. Preparation of rGST-bound Sepharose 4B Gel was performed according to the operating instructions of Pharmacia K. K.

The reaction of the above-eluted fraction with GST was carried out according to ELISA method as in (3-1). Here, RGST was bound to a microplate in place of rRCAS1-GST in (3-1) and the eluted fraction was added thereto. Thereafter, washing, labeling and the like were carried out and absorbance was measured according to the similar procedures to those of (3-1). After the removal of the reactivity with GST was confirmed by sufficiently washing with PBS, the immunoglobulin bound to the gel was eluted with 0.17M glycine-HCl buffer, pH2.3. In order to prevent denaturation of immunoglobulin (reduction in antibody activity), the eluted solution was neutralized by rapidly adding an 1/10 amount of 1M Tris-HCl buffer, pH9.0.

EXAMPLE 4

Measurement of RCAS1 in Serum (4-1) Preparation of Monoclonal Antibody-Solid Phased Microplate The 22-1-1 monoclonal antibody obtained in the (1-4) was adjusted to the concentration of 5 µ/ml with 0.1M carbonate buffer, pH 9.0, each 10 µl of which was added to each well of a 96-well microplate "Maxisoap" manufactured by Nunc and allowed to stand to react at 4° C. for 20 hours. Thereafter, the antibody solution was removed, and each 200 µl of PBS containing 1% BSA and 5% sucrose, which was allowed to stand at room temperature (20–25° C.) for 2 hours to perform blocking. After the blocking solution was removed, the plate was air dried to obtain 22-1-1 monoclonal antibody-solid phased microplate. This solid phased antibody together with a desicator was stored by sealing.

(4-2) Preparation of Labeled Antibody

IgG fraction was purified from the anti-RCAS1 polyclonal solution obtained in the (3-2) using DEAE cellulose column. Ficin was added to this purified IgG fraction at a rate of 0.056 U per 1 mg IgG to react at 37° C. for 8 hours, followed by gel filtration using Ultrogel ACA44 to obtain F(ab)'2 fraction. This F(ab)'2 fraction was labeled with peroxidase by a maleimide method to obtain peroxidase-labeled antibody. Labeling method was carried out according to "Enzyme Immunoassay Method, the third edition" authored by Eiji Ishikawa published by Igakushoin.

(4-3) Measurement of RCAS1 in a Specimen

A specimen serum was 10× diluted with PBS containing 10% normal rabbit serum and, each 100 µl of which was added to each well of a microplate (solid phased microplate obtained in (4-1)). As a standard, RCAS1 was diluted with the same buffer to an arbitral concentration (1 U/mL), which was fold-diluted and the same procedures were performed as in the specimen, and 100 µl was added similarly.

Figure 2:
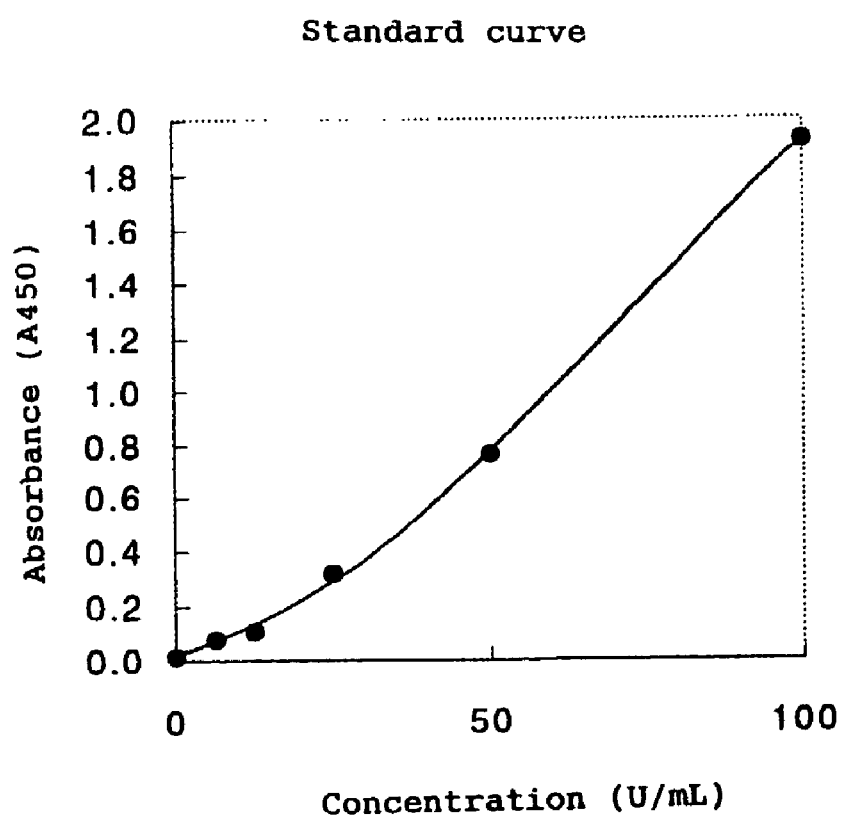
FIG. 2 is a standard curve used for quantitating RCAS1 in serum.

After the microplate thus prepared was reacted while shaking mildly for 1 hour at room temperature (20–25° C.), a sample of each well was removed and, subsequently, each well was washed by adding and removing 30 µl of PBS containing 0.1% Tween 20 to and from each well. This washing procedure was performed 5 times. After the washing solution was removed, the peroxidase-labeled antibody obtained in (4-2) was diluted to 1 µg/ml with 1% BSA, 0.79% NaCl, 0.1% p-hydroxyphenyl acetic acid, 20 mM HEPES buffer, pH 7.2, each 100 µl of which was added to each well and reacted at room temperature (20–25° C.) for 1 hour while mildly shaking. After the reaction, the reaction was washed again with PBS containing 0.1% Tween 20 as described above. Then, the washing solution was removed, each 100 µl of a solution obtained by mixturing an equal amount of 10 mM solemn citrate containing 1.6 mM 3,3', 5,5'-tetramethylbenzitine dihydrochloride, 20% N,N-dimethylformamide and 1.25% polyethylene glycol 4000 and 10 mM citric acid solution containing 10 mM hydrogen peroxide was added to each well to react while mildly shaking at room temperature (20–25° C.) for 30 minutes. Subsequently, 100 µl of 1.5N phosphoric acid was added to each well to stop the reaction and absorbance of each well at wavelength 450 nm was measured. The concentration of RCAS1 in a specimen was read using a standard curve (see a graph in FIG. 2) produced from the concentration and absorbance of a standard.

Figure 4:
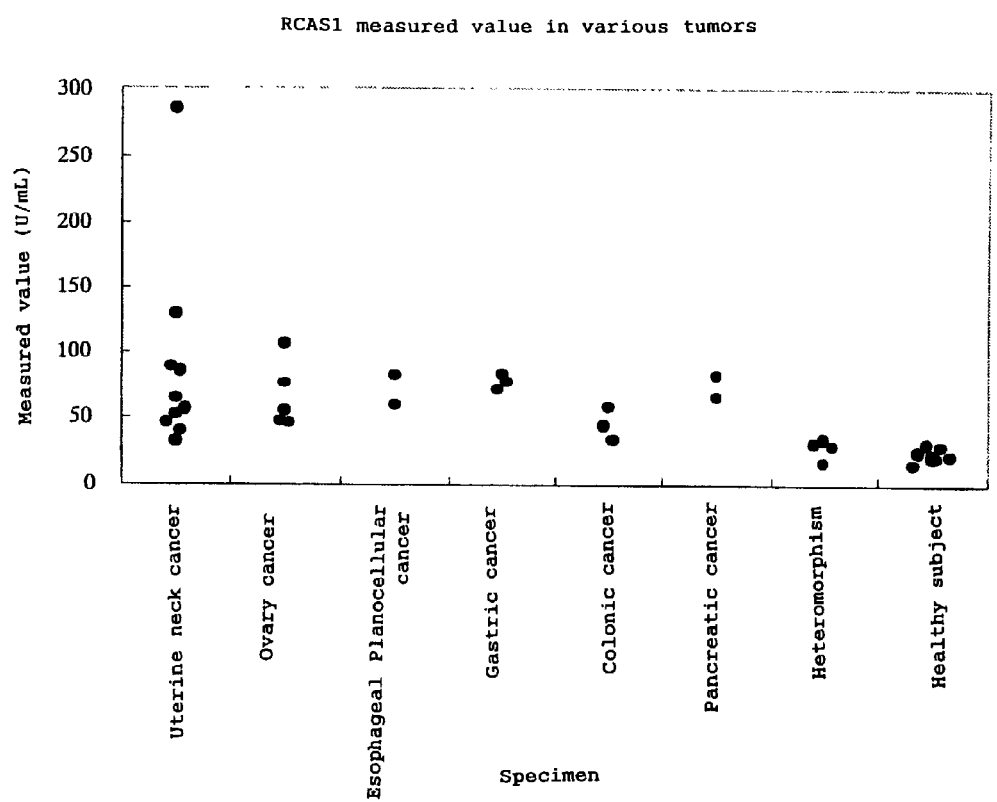
FIG. 4 is a graph in which the results of quantitation of RCAS1 in each cancer patient are plotted.

This measuring system was used to measure 10 examples of healthy individuals, 9 examples of uterine neck cancer patients, 5 examples of ovary cancer patients, 2 examples of esophageal planocellular cancer patients, 3 examples of gastric cancer, 3 examples of colonic cancer patients, 2 examples of pancreatic cancer patients, and 4 examples of dysplsia aberration patients. The results thereof are shown in FIG. 3 and FIG. 4. As shown in FIG. 3 and FIG. 4, the concentration of RCAS1 in each cancer patient's serum is significantly increased in serum of each cancer patient as compared with that of healthy individuals. That is, it is shown that a wide range of cancers can be found according to the measuring method of this Example. In addition, a difference in the measured values is recognized between dysplasia aberration patients and each cancer patients and, thus, it is shown that the progressing state of cancers can be predicted. Like this, according to the measuring method of this Example, a wide range of cancers can be found by rapid and simple method and the effective means by which progressing state of cancers is known is provided.

EXAMPLE 5

Measurement of Anti-RCAS1 Antibody in Serum (5-1) Preparation of RCAS1-Solid Phased Microplate The RCAS1-GST fusion protein obtained in the (2—2) was adjusted to the concentration of 5 µl/ml with 0.1M carbonate buffer, pH 9.0, each 10 µl of which was added to each well of a 96-well microplate "Maxisoap" manufactured by Nunc to allow to react at 4° C. for 20 hours. Thereafter, the solution was removed, each 200 µl of PBS containing 1% BSA and 5% sucrose was added to each well, which was allowed to stand at room temperature (20–25° C.) for 2 hours to perform blocking. After blocking solution was removed, the plate was air dried to obtain RCAS1-solid phased microplate. This solid phased microplate together with desicator was stored by sealing.

(5-2) Measurement of Anti-RCAS1 Antibody in Specimen

A specimen serum was 10× diluted with PBS containing 10% normal rabbit serum, 100 µl of which was added to each well of the solid phased microplate in (5-1). As a standard, serum of anti-RCAS1 antibody-positive patient was adjusted to an arbitral concentration with the same buffer (1 U/mm), which was fold-diluted and the same procedures were performed as in a specimen, and 100 µl was added similarly.

The microplate thus prepared was reacted at room temperature (20–25° C.) for 1 hour while mildly shaking, a sample of each well was removed and, subsequently, each well was washed by adding and removing 30 µl of PBS containing 0.1% Tween 20 to and from each well. This washing procedure was performed 5 times. After the washing solution was removed, labeled anti-human immunoglobulin antibody (manufactured by Medical and Biological Laboratories, Co., Ltd.) was added to each well, which was reacted at room temperature (20–25° C.) for 1 hour while shaking mildly. After the reaction, each well was washed again with PBS containing 0.1% Tween 20 as described above. Then, washing solution was removed, each 100 µl of a solution obtained by mixing an equal amount of 10 mM sodium citrate solution containing 1.6 mM 3,3',5,5'-tetramethylpenzidene dihydrochloride, 20% N,N-dimethylformamide, and 1.25% polyethylene glycol 4000 and 10 mM citric acid solution containing 10 mM hydrogen peroxide was added to each well, which was reacted at room temperature (20–25° C.) for 30 minutes while shaking mildly. Subsequently, 100 μl of 1.5N phosphoric acid was added to each well to stop the reaction, absorbance of each well of wavelength 450 nm was measured, and anti-RCAS1 antibody was quantitated using a standard curve obtained from absorbance of a standard.

EXAMPLE 6

Measurement of RCAS1 Receptor in Serum

Each test serum was 10× diluted with PBS, to this was added rRCAS1-GST obtained in the (2—2), which was reacted at room temperature (20–25° C.) for 1 hour while shaking mildly. As a standard, serum of RCAS1 receptor-positive patient was adjusted to an arbitral concentration by diluting with the same buffer (1 U/ml), which was fold-diluted and the same procedure was performed as in the specimen, and 100 μl was added similarly. Then, each 100 μl of each reaction solution was added to each well of 22-1-1 monoclonal antibody-solid phased microplate obtained in the (4-1) and, subsequently, rRCAS1-GST labeled with peroxidase obtained in the (2—2) was added to each well. The microplate thus prepared was reacted at room temperature (20–25° C.) for 1 hour while mildly shaking, a sample of each well was removed and, subsequently, each well was washed by adding and removing 30 μl of PBS containing 0.1% Tween 20 to and from each well. This washing procedure was performed 5 times. Then each 100 μl of a solution obtained by mixing an equal amount of 10 mM sodium citrate solution containing 1.6 mM 3,3',5,5'-tetramethylbenzydine dihydrochlolide, 20% N,N-dimethylformamide, and 1.25% polyethylene glycol 4000 and a 10 mM citric acid solution containing 10 mM hydrogen peroxide was added to each well, which was reacted at room temperature (20–25° C.) for 30 minutes while mildly shaking. Subsequently, each 100 μl 1.5M phosphoric acid was added to each well to stop the reaction, and a labeled amount of labeled rRCAS1-GST bound to the solid phased antibody was measured by absorbance of each well at wavelength 450 nm.

EXAMPLE 7

Detection of RCAS1 Receptor in Various Cells

The binding property of rRCAS1-GST obtained in the (2—2) with various cells was examined. First, 1.0 μg/ml rGST or rRCAS1-GST fusion protein was added to $1 \times 10^3$ of various cells and incubated on ice for 30 minutes. After incubation, the sample was washed 3 times and, subsequently, 0.5 μg of affinity-purified rabbit anti-GST antibody (manufactured by Southern Biotech) was added to each sample to incubate. This was reacted with +PE labeled anti-rabbit IgG antibody (goat F(ab')2IgG) purified with human and mouse serum and analyzed with Coulter Epics XL flow cytometer (manufactured by Coulter Corporation).

As a result, it was found that rRCAS1-GST fusion protein is bound to the surface of many human and mouse cell strain such as K562 (human chronic myelogeneous leukemia), CCRF-CEM (human T lymphoblast), Ramos (Burkitt lymphoma), WI-38 (human diploid cell line), IMR-90 (human diploid cell line), 293 (human transformed embrional kidney cell line), mouse L cell and NIH3T 3 cell.

Further, upon incubation by adding rRCAS1-GST fusion protein to each cell, a sample to which 22-1-1 antibody obtained in (1-4) had been added together was prepared, and the ability of 22-1-1 antibody to inhibit the binding of rRCAS1-GST fusion protein and each cell was investigated.

As a result, it was found the binding of rRCAS1-GST fusion protein to each cell is inhibited by the addition of 22-1-1 antibody.

EXAMPLE 8

Immunoprecipitation of RCAS1-receptor molecule

K562 (human chronic myelogenious leukemia cell line) and U937 cell (a human histiocytic leukemia cell line) were labeled with sulfo-NHS biotin (manufactured by Pierce) and incubated with rRCAS1-GST fusion protein obtained in the (2—2). As a control, in place of rRCAS1-GST fusion protein, rGST was added to each cell to incubate similarly. RGST, which had been prepared according to the same method as that for rRCAS1-GST fusion protein in (2—2) was used. After reaction, each cell was dissolved, which was reacted with magnetic beads coated with affinity-purified rabbit anti-GST (IgG). The precipitates were eluted into β-mercaptoethanol-containing sample buffer, separated with 12% SDS-PAGE and assessed by Western blot using peroxidase-labeled streptavidin ECL (manufactured by Amersham Medical Ltd.).

Figure 5:
FIG. 5 shows the results from analysis by Western blotting of a RCAS1 receptor molecule obtained by an immunoprecipitation method.

The results of Western blot are shown in FIG. 5. In FIG. 5, lane 1, lane 2, lane 3 and lane 4 are, in this order, the results of samples in which K562 and rGST, K562 and rRCAS1-GST fusion protein, U937 and rGST, U937 and rRCAS1-GST fusion protein were incubated. From FIG. 5, a band of a molecular weight 25 kDa was observed in lane 2 and, from K562 cell, a molecule of a molecular weight 25 kDa was identified as rRCAS1-bound protein.

EXAMPLE 9

Preparation of Biotin-Labeled Antibody

An aldehyde was introduced into the monoclonal antibody 22-1-1 obtained in Example 1 by oxidation with sodium metaperiodate, which was bound with biotin hydrazide to obtain a biotinated antibody. Specifically, 1 ml of an ice-cooled metaperiodic acid solution was added to 1 ml of the ice-cooled monoclonal antibody 22-1-1, which was mixed well and subjected to an oxidation reaction in the dark place at 0° C. for 30 minutes. Thereafter, glycerol was added thereto to the final concentration of 15 mM, which was incubated at 0° C. for 5 minutes to stop the oxidation reaction. This solution was dialyzed against a 0.1M sodium acetate buffer (pH5.5) overnight, and biotin hydrazide was added to the final concentration of 5 mM to stir at room temperature for 2 hours. The unreacted molecules were removed from this by dialysis to obtain a biotin-labeled antibody.

EXAMPLE 10

Study of Influence of the Sialidase Treatment in Measuring RCAS1

An amount of RCAS1 in sera of patients with various cancers was measured using the ELISA method. As a specimen to be subjected to the ELISA method, 23 serum specimens with patients with pulmonary cancer, 3 serum specimens of patients with ovarian cancer, 5 serum specimens of patients with colonic cancer, 1 serum specimen of a patient with breast cancer, the supernatant of SiSo cell culture, and 7 specimens of healthy subjects were used. A group in which each specimen was treated with sialidase in advance (sialidase-treated group) and a group in which no sialidase treatment is performed (control group) were compared, and influence of the sialidase treatment on RCAS1 measurement was studied.

(Sialidase Treatment)

A method of the sialidase treatment was performed as follows: First, 4 μl of a specimen and 46 μl of a buffer for digesting sialidase were mixed, and incubated at 37° C. for 10 minutes. Then, 50 μl of a sialidase solution (obtained by dissolving sialidase (manufactured by Sigma) in a buffer for digesting sialidase to 20 mU/mL) to the reaction solution, which was incubated at 37° C. for 1 hour. Thereafter, 100 μl of 2-fold concentrated TBS-T (pH 7.5) was added thereto. The resulting solution was subjected to the following ELISA method.

(ELISA Method)

Each specimen after the sialidase treatment was diluted with 2-fold concentrated TBS-T (pH 7.5) to final 50-fold, each 100 μl of which was added to each well of the solid-phased microplate obtained in Example 4. In a control group, serum of each cancer patient was diluted with 2-fold concentrated TBS-T (pH 7.5) to final 50-fold, which was dispensed.

Figure 7:
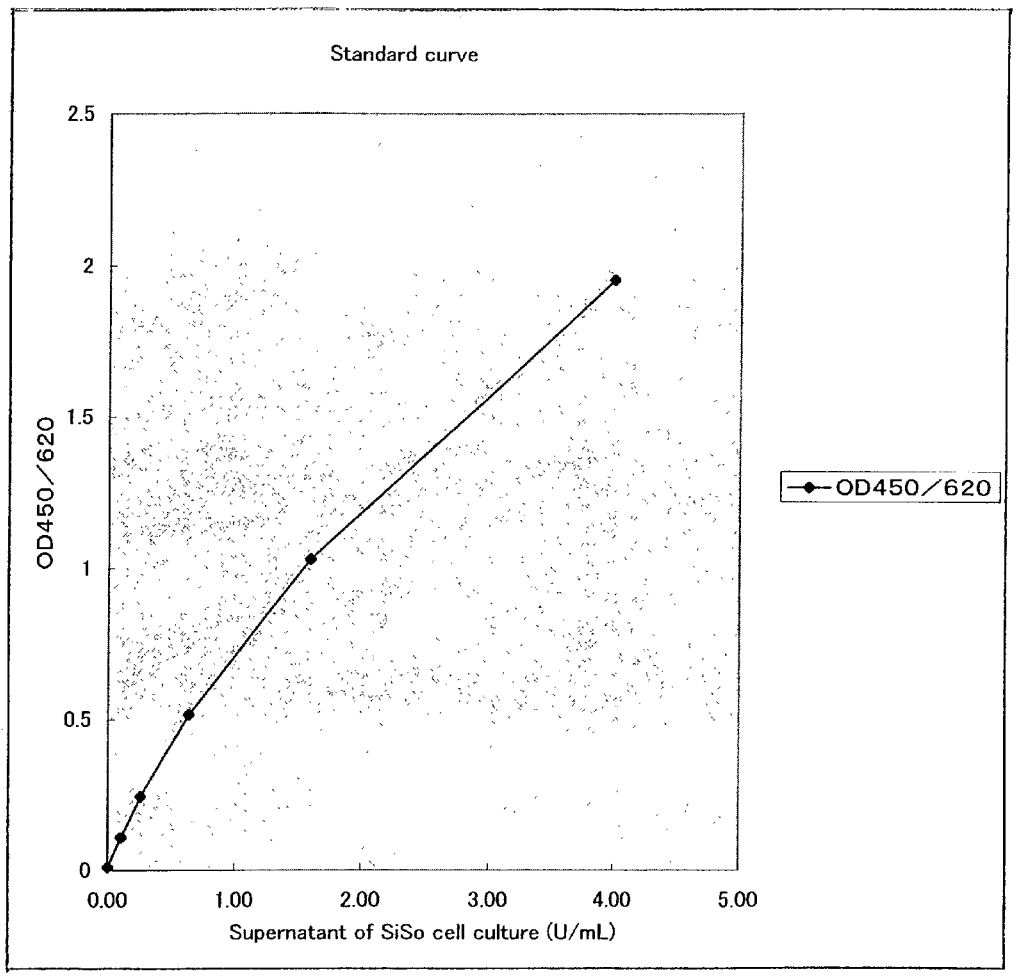
FIG. 7 is a standard curve produced by using a supernatant of the SiSo cell culture.

Then, the microplate was reacted at room temperature (20–25° C.) for 1 hour. After the solution in each well was removed, each well was washed with 300 μl of PBS containing 0.1% tween20. This washing procedure was performed five times. After washing, the biotin-labeled antibody obtained in Example 9 was diluted with the TBS buffer (pH 7.5) containing BSA to 0.2 μg/mL, and each 100 μl of the dilution was added to each well to react at room temperature (20–25° C.) for 1 hour while mildly stirring. After the reaction solution was removed from each well, each well was washed with PBS containing 0.1% tween20 as described above. After washing solution was removed, 100 μl of a streptoavidin-peroxidase solution was added to react at room temperature for 1 hour while mildly stirring. After the reaction solution was removed from each well, each well was washed with PBS containing 0.1% tween20. Subsequently, each 100 μl of a solution of orthophenylenediamine which is a chromogenic substrate (to which hydrogen peroxide was added to final concentration of 0.03% immediately before use) was added to each well to react at room temperature for 3–5 minutes. Finally, each 100 μl of a 20% phosphoric acid solution was added to stop color development. The absorbances at a wavelength of 450 nm and 620 nm of the thus obtained each well were measured. In addition, a standard curve was produced (FIG. 7) based on the measured value obtained by treating the supernatant of SiSo cell culture as described above, and this was used to obtain the concentration of RCAS1 in each specimen. The RCAS1 amount contained in 1 ml of the SiSo cell supernatant was adopted as 100 U.

Figure 9:
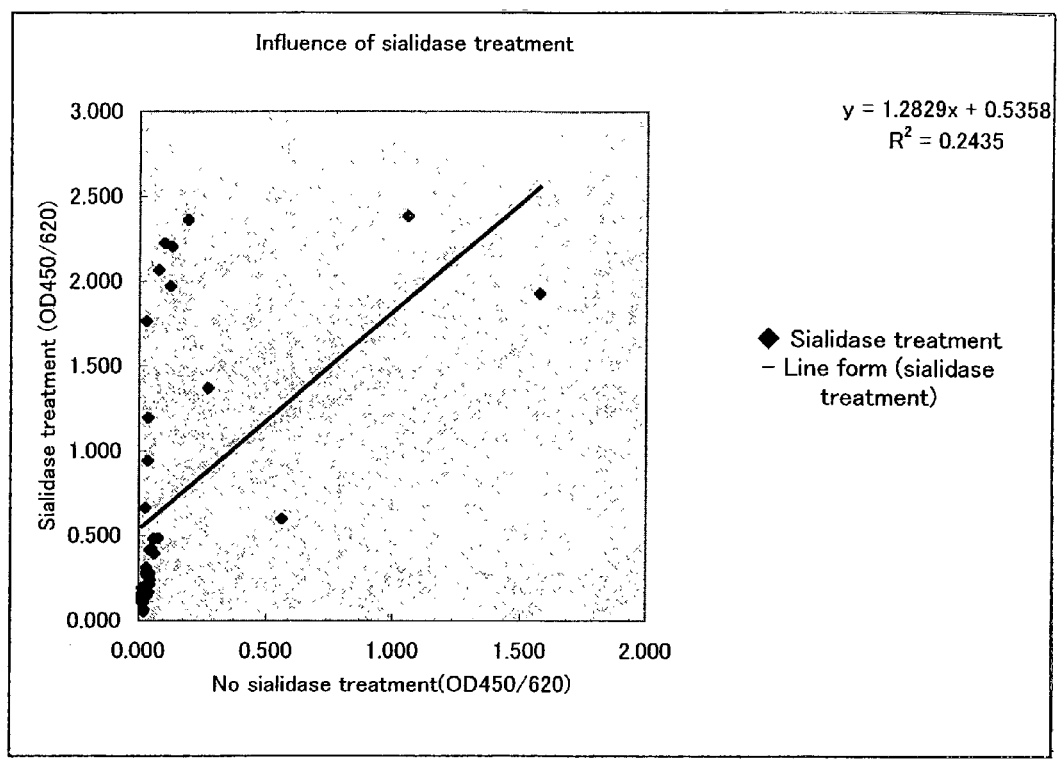
FIG. 9 shows graphically a table of the left column of FIG. 8.

A table summarizing the measurement results is shown in FIG. 8. The left column of FIG. 8 is a table summarizing the value of OD450/620 of each specimen, and the right column is a table summarizing the concentration (U/mL) calculated from a standard curve. As seen from each table in FIG. 8, the measured value was risen in all specimens of a cancer patient by performing the sialidase treatment. In particular, a remarkable rise in the measured value was recognized in the colonic cancer specimen and the pulmonary cancer specimen. FIG. 9 shows graphically the table of the left column of the FIG. 8.

EXAMPLE 11

Study on the Relationship Between Sialidase Treatment and Clinical Stage

Using the serum of a pulmonary cancer patient, the relationship between a change in the ELISA measured value by performing the sialidase treatment and clinical stage (stage of disease) was studied.

Five specimens of the serum of a pulmonary cancer patient were prepared per clinical stage (stages 1–4), and the measured values were compared between a group in which detection is performed by the ELISA method after the sialidase treatment (sialidase-treated group) and a group in which detection was performed by the ELISA method without performing the sialidase treatment (control group). The procedures for the sialidase treatment and the ELISA method were the same as those in Example 10.

Figure 11:
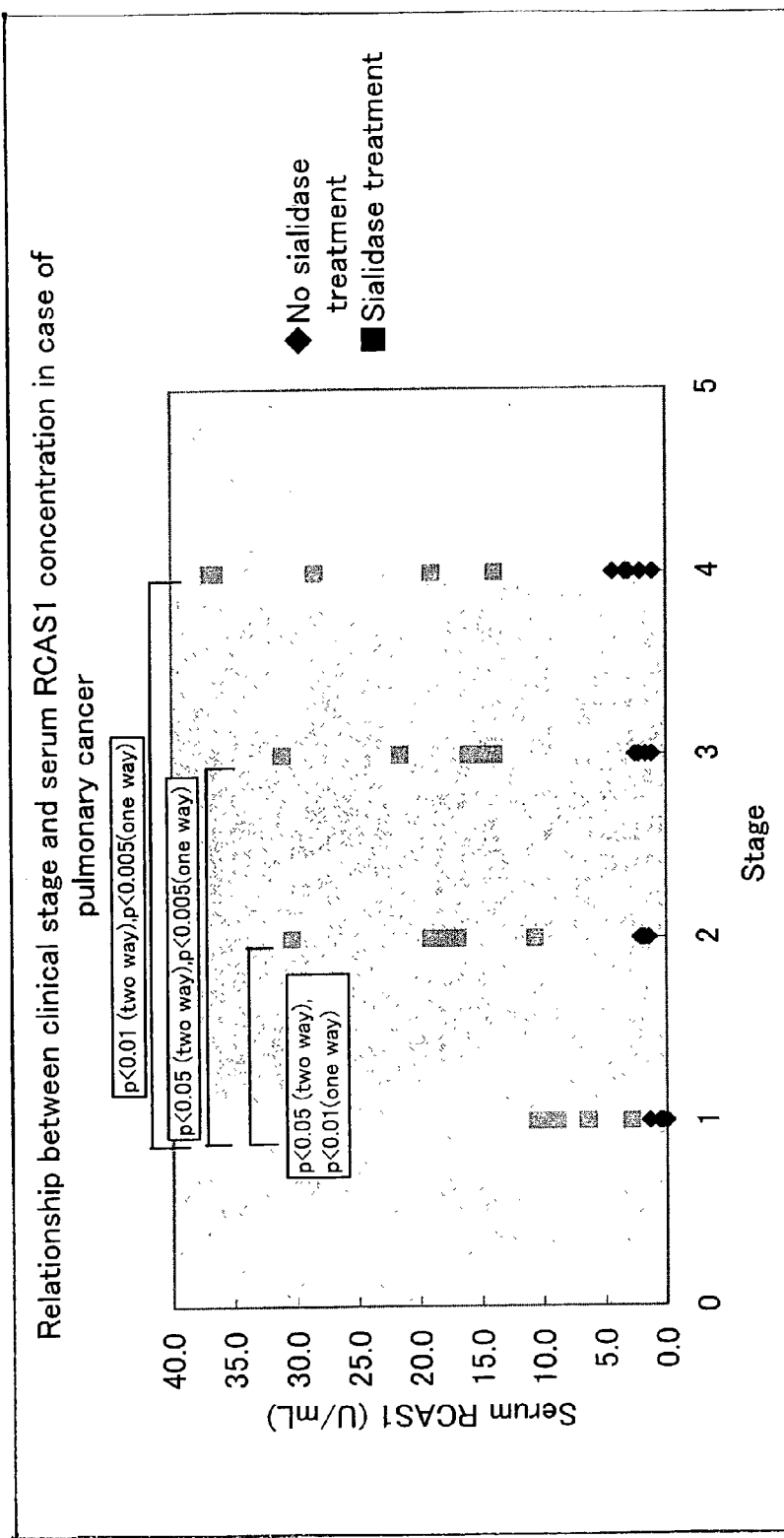
FIG. 11 shows graphically the table of FIG. 10.

A table summarizing measurement results is shown in FIG. 10. In addition, a graph plotting respective measured values is shown in FIG. 11. In these table and graph, the concentration (U/mL) calculated using a standard curve produced in Example 10 was used.

As shown in FIGS. 10 and 11, it is recognized that the measured value is risen by the sialidase treatment. As a result, a difference in the RCAS1 concentration (concentration calculated from the measured value) between a specimen classified into stages 24 and a specimen classified into stage 1 was made clearer. On the other hand, there is recognized a tendency that as the stage grows higher, the RCAS1 concentration is increased. This suggests a possibility that progress of the disease can be monitored by measuring the RCAS1 amount with time and, from this, it is considered that usefulness of RCAS1 as a tumor marker is extremely high.

EXAMPLE 12

Measurement of the RCAS1 Concentration in Serum of Patients with Various Cancers Using the measuring system of Example 10 (that is, measuring system in which the ELISA method is performed after the sialidase treatment), the RCAS1 concentrations in the serum of a healthy subject and in the serum of a cancer patient were measured.

Figure 12:
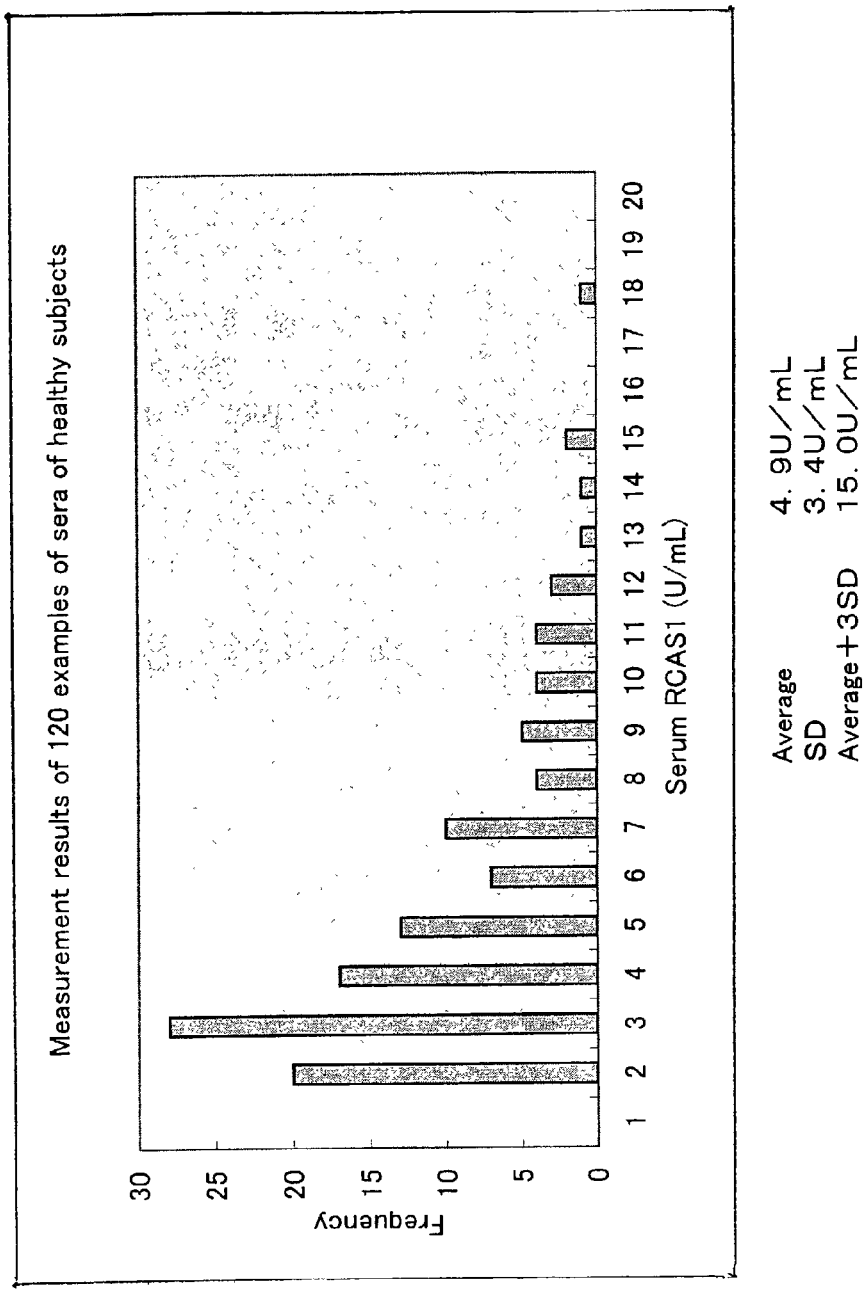
FIG. 12 is a graph summarizing the results of measurement of an amount of RCAS1 in 200 serum specimens of healthy subjects using the ELISA method.

First, 200 serum specimens of healthy subjects were treated with sialidase by the method described in Example 10. That is, 46 μl of a buffer for digesting sialidase was mixed into 4 μl of each specimen, which was incubated at 37° C. for 10 minutes. Then, 50 μl of a sialidase solution (obtained by dissolving sialidase (manufactured by Sigma) in a buffer for digesting sialidase to 20 mU/mL) was added to the reaction solution, which was incubated at 37° C. for 1 hour. Thereafter, 100 μl of 2-fold concentrated TBS-T (pH 7.5) was added. The thus obtained solution was used to perform the ELISA method by the method described in Example 10, and the RCAS1 concentration in each specimen was obtained by using a standard curve produced using the supernatant of the SiSo cell culture. A graph summarizing measurement results is shown in FIG. 12. An average and SD (standard deviation) were obtained to be 4.9 U/mL and 3.4 U/mL, respectively.

Then, according to the same manner, the RCAS1 concentrations in sera of patients with various cancers (20 serum specimens of patients with dermal cancer, 42 serum specimens of patients with ovarian cancer, 25 serum specimens of patients with pulmonary cancer, 29 serum specimens of patients with colonic cancer, 29 serum specimens of patients with breast cancer, 20 serum specimens of patients with prostate cancer, 20 serum specimens of patients with endometrium cancer, 20 serum specimens of patients with testis cancer, 20 serum specimens of patients with renal cancer) were measured. The measurement results were added up per a diagnosed name, and Mean, SD value (standard deviation), Median, Minimum and Maximum of each diagnosed name were obtained. On the other hand, from the aforementioned measurement results of specimens of healthy subjects, Mean+3SD, that is, 15 U/mL in specimens of healthy subjects was set at a cutoff value, and a specimen having a higher value than this value was determined to be positive. A table in FIG. 13 summarizes each value of Mean and the like, number of positive specimens and positive rate per diagnosed name. In addition, a graph in FIG. 14 is a graph plotting the RCAS1 concentration of each specimen per diagnosed name.

From the table in FIG. 13, it can be seen that measurement of each disease is possible at a high positive rate except for endometrium cancer. In particular, a positive rate is very high in dermal cancer, pulmonary cancer, colonic cancer and renal cancer and, thus, it was confirmed that the method of the present Example is extremely effective for diagnosing these diseases.

EXAMPLE 13

Comparison Between RCAS1 and Other Tumor Markers

Then, by using various pancreatic diseases as a measurement subject, from a viewpoint of the sensitivity, the specificity and the accuracy, RCAS1 was compared with CA19-9 known to be a tumor marker. First, using 20 serum specimens of patients with pancreatic excretory ductal adenocarcinoma (PDA), 6 serum specimens of patients with pancreatic intraductal papillary (IPA) adenoma, 10 serum specimens of patients with chronic pancreatitis (CP), 5 serum specimens of patients with acute pancreatitis (AP) and 5 serum specimens of patients with autoimmune pancreatitis (AIP), the sialidase treatment and the ELISA method were performed by the method described in Example 10 to measure the RCAS1 concentration in each specimen. The RCAS1 concentration (U/mL) was obtained by utilizing a standard curve produced using the supernatant of the SiSo cell culture. The measurement results were added up per diagnosed name, and Mean (average value), SD (standard deviation), Range (Minimum and Maximum) and Median were obtained. In addition, the cutoff value was set at 15 U/mL, and a specimen having a higher value than this value was determined to be positive. A table in FIG. 15 summarizes each value such as mean and the like, number of positive specimens and positive rate per diagnosed name. In addition, a graph in FIG. 16 is a graph plotting the RCAS1 concentration of each specimen per diagnosed name.

On the other hand, regarding CA19-9, using the measurement values described in datasheet, Mean (average value), SD (standard deviation), Ragne (Minimum and Maximum), Median, number or positive specimens and positive rate were obtained, which were summarized in a table in FIG. 17. Based on data shown in this table and the table in FIG. 15, the sensitivity, the specificity and the accuracy of RCAS1 and CA19-9 were obtained (table in FIG. 18). The sensitivity was obtained as a ratio of specimens determined to be positive among pancreatic excretory ductal adenocarcinoma and pancreatic intraductal papillary adenoma (correctly diagnosed prevalence). Similarly, the specificity was obtained as a ratio of specimens determined to be negative among chronic pancreatitis and acute pancreatitis as well as autoimmune pancreatitis (correctly diagnosed nondisease rate), and the accuracy was obtained as a sum of both.

Positive rate=$(17+5)/(20+6)=22/26=84.6\%$=approximately 85%

Specificity=$(10+4+5)/(10+5+5)=19/20=95\%$

Accuracy=$(22+19)/(26+20)=41/46=89.1\%$=approximately 89%

From the table in FIG. 15, it can be seen that RCAS1 is detected at a very high positive rate in pancreatic excretory ductal adenocarcinoma and pancreatic intraductal papillary adenoma. In addition, it can be seen that a positive rate for RCAS1 is greatly different between diagnosed names, and the specificity and the accuracy are much excellent as compared with CA19-9 (see FIG. 18). From this, it is considered that RCAS1 can be utilized as a tumor marker having the high specificity.

The present invention is not limited to the above embodiment and Examples. A variety of variation aspects are included in the present invention as far as they are not departed from the description of the claims and in a range which can be readily contemplated by those skilled in the art.

What is claimed is:

1. A method for immunologically measuring RCAS1 which is recognized by a monoclonal antibody produced by a hybridoma having accession number of FERM BP-7002, which comprises:

a step of reacting a specimen with a solid phased RCAS1 antibody obtained by binding to an insoluble support a first anti-RCAS1 antibody that specifically binds to RCAS1 to form a first reaction product when said anti-RCAS1 antibody binds RCAS1, reacting said first reaction product with a second anti-RCAS1 antibody labeled with a labeling substance to form a labeled first reaction product when said second anti-RCAS1 antibody binds RCAS1 of the first reaction product, and measuring a labeled amount of the produced first reaction product;

a step of producing a calibration curve by reacting said solid phased anti-RCAS1 antibody with a supernatant of SiSo cell culture or body fluid obtained from a cancer patient, which contains a second RCAS1 as a standard substance to form a second reaction product when said anti-RCAS1 antibody binds the second RCAS1, and measuring a labeled amount of the produced second reaction product; and a step of quantitating RCAS1 in the specimen from a labeled amount of said first reaction product and said calibration curve; and wherein said first anti-RCAS1 antibody is a monoclonal antibody which recognizes RCAS1 produced by a hybridoma having accession number of FERM BP-7002.

2. A method for immunologically measuring RCAS1 which is recognized by a monoclonal antibody produced by a hybridoma having accession number of FERM BP-7002, which comprises the following steps a) to g):

a) a step of reacting a specimen with a first anti-RCAS1 antibody that specifically binds to RCAS1 to form a first reaction product when said anti-RCAS1 antibody binds RCAS1;

b) a step of labeling the first reaction product produced in said step a);

c) a step of measuring a labeled amount of the labeled said first section product;

d) a step of reacting said first anti-RCAS1 antibody with a supernatant of SiSo cell culture or body fluid obtained from a cancer patient, which contains a second RCAS1 as a standard substance to form a second reaction product when said anti-RCAS1 antibody binds the second RCAS1;

e) a step of labeling the second reaction product produced in said step d);

f) a step of producing a calibration curve by measuring a labeled amount of the labeled said second reaction product; and g) a step of quantitating RCAS1 in said specimen from a labeled amount of said first reaction product and said calibration curve; and wherein said first anti-RCAS1 antibody is a monoclonal antibody which recognizes RCAS1 produced by a hybridoma having accession number of FERM BP-7002.

3. A method for immunologically measuring RCAS1 according to claim 1, wherein said labeling substance is selected from the group consisting of peroxidase, β-D-galactosidase, microperoxidase, alkaline phosphatase, biotin and a radioactive substance.

4. A method for immunologically measuring RCAS1 according to claim 2, wherein said specimen is serum.

5. A method for immunologically measuring RCAS1 which is recognized by a monoclonal antibody produced by a hybridoma having accession number of FERM BP-7002, which comprises the following steps a) and b):

a) a step of competitively reacting an anti-RCAS1 antibody that specifically binds to RCAS1 with a specimen and a supernatant of SiSo cell culture or body fluid obtained from a cancer patient, which contains a second RCAS1 labeled by a labeling substance in advance to form a labeled reaction product when said anti-RCAS1 antibody binds labeled RCAS1;

b) a step of measuring a labeled amount of the reaction product produced in the step a); and wherein said anti-RCAS1 antibody is a monoclonal antibody which recognizes RCAS1 which is produced by a hybridoma having accession number of FERM BP-7002.

6. A method for immunologically measuring RCAS1 which is recognized by a monoclonal antibody produced by a hybridoma having accession number of FERM BP-7002, which comprises:

a step of reacting a specimen with a solid phased antibody obtained by binding to an insoluble support a monoclonal antibody which recognizes RCAS1 to form a first reaction product, wherein said monoclonal antibody is produced by hybridoma having accession number FERM BP-7002 and, thereafter, reacting said first reaction product with an anti-RCAS1 antibody labeled with a labeling substance and measuring a labeled amount of the produced first reaction product;

a step of producing a calibration curve by reacting said solid phased antibody with a supernatant of SiSo cell culture or body fluid obtained from a cancer patient, which contains a second RCAS1 and, thereafter, reacting with said labeled anti-RCAS1 antibody and measuring a labeled amount of the produced second reaction product; and a step of quantitating RCAS1 contained in said specimen from a labeled amount of said first reaction product and said calibration curve.

* * * * *

SEQUENCE LISTING

<160> NUMBER OF SEQ ID NOS: 2

<210> SEQ ID NO 1
<211> LENGTH: 642
<212> TYPE: DNA
<213> ORGANISM: Homo sapiens
<220> FEATURE:
<221> NAME/KEY: CDS
<222> LOCATION: (1)..(642)

<400> SEQUENCE: 1

```
atg gcc atc acc cag ttt cgg tta ttt aaa ttt tgt acc tgc cta gca      48
Met Ala Ile Thr Gln Phe Arg Leu Phe Lys Phe Cys Thr Cys Leu Ala
 1               5                  10                  15
```

-continued

```
aca gta ttc tca ttc cta aag aga tta ata tgc aga tct ggc aga gga        96
Thr Val Phe Ser Phe Leu Lys Arg Leu Ile Cys Arg Ser Gly Arg Gly
            20                  25                  30 cgg aaa tta agt gga gac caa ata act ttg cca act aca gtt gat tat       144
Arg Lys Leu Ser Gly Asp Gln Ile Thr Leu Pro Thr Thr Val Asp Tyr
        35                  40                  45 tca tca gtt cct aag cag aca gat gtt gaa gag tgg act tcc tgg gat       192
Ser Ser Val Pro Lys Gln Thr Asp Val Glu Glu Trp Thr Ser Trp Asp
    50                  55                  60 gaa gat gca ccc acc agt gta aag atc gaa gga ggg aat ggg aat gtg       240
Glu Asp Ala Pro Thr Ser Val Lys Ile Glu Gly Gly Asn Gly Asn Val
65                  70                  75                  80 gca aca caa caa aat tct ttg gaa caa ctg gaa cct gac tat ttt aag       288
Ala Thr Gln Gln Asn Ser Leu Glu Gln Leu Glu Pro Asp Tyr Phe Lys
                85                  90                  95 gac atg aca cca act att agg aaa act cag aaa att gtt att aag aag       336
Asp Met Thr Pro Thr Ile Arg Lys Thr Gln Lys Ile Val Ile Lys Lys
            100                 105                 110 aga gaa cca ttg aat ttt ggc atc cca gat ggg agc aca ggt ttc tct       384
Arg Glu Pro Leu Asn Phe Gly Ile Pro Asp Gly Ser Thr Gly Phe Ser
        115                 120                 125 agt aga tta gca gct aca caa gat ctg cct ttt att cat cag tct tct       432
Ser Arg Leu Ala Ala Thr Gln Asp Leu Pro Phe Ile His Gln Ser Ser
    130                 135                 140 gaa tta ggt gac tta gat acc tgg cag gaa aat acc aat gca tgg gaa       480
Glu Leu Gly Asp Leu Asp Thr Trp Gln Glu Asn Thr Asn Ala Trp Glu
145                 150                 155                 160 gaa gaa gaa gat gca gcc tgg caa gca gaa gaa gtt ctg aga cag cag       528
Glu Glu Glu Asp Ala Ala Trp Gln Ala Glu Glu Val Leu Arg Gln Gln
                165                 170                 175 aaa cta gca gac aga gaa aag aga gca gcc gaa caa caa agg aag aaa       576
Lys Leu Ala Asp Arg Glu Lys Arg Ala Ala Glu Gln Gln Arg Lys Lys
            180                 185                 190 atg gaa aag gaa gca caa cgg cta atg aag aag gaa caa aac aaa att       624
Met Glu Lys Glu Ala Gln Arg Leu Met Lys Lys Glu Gln Asn Lys Ile
        195                 200                 205 ggt gtg aaa ctt tca taa                                               642
Gly Val Lys Leu Ser
    210
```

<210> SEQ ID NO 2
<211> LENGTH: 213
<212> TYPE: PRT
<213> ORGANISM: Homo sapiens

<400> SEQUENCE: 2

Met Ala Ile Thr Gln Phe Arg Leu Phe Lys Phe Cys Thr Cys Leu Ala
1               5                   10                  15

Thr Val Phe Ser Phe Leu Lys Arg Leu Ile Cys Arg Ser Gly Arg Gly
            20                  25                  30

Arg Lys Leu Ser Gly Asp Gln Ile Thr Leu Pro Thr Thr Val Asp Tyr
        35                  40                  45

Ser Ser Val Pro Lys Gln Thr Asp Val Glu Glu Trp Thr Ser Trp Asp
    50                  55                  60

Glu Asp Ala Pro Thr Ser Val Lys Ile Glu Gly Gly Asn Gly Asn Val
65                  70                  75                  80

Ala Thr Gln Gln Asn Ser Leu Glu Gln Leu Glu Pro Asp Tyr Phe Lys
                85                  90                  95

Asp Met Thr Pro Thr Ile Arg Lys Thr Gln Lys Ile Val Ile Lys Lys

-continued

```
                        100                     105                     110
Arg Glu Pro Leu Asn Phe Gly Ile Pro Asp Gly Ser Thr Gly Phe Ser
        115                     120                     125

Ser Arg Leu Ala Ala Thr Gln Asp Leu Pro Phe Ile His Gln Ser Ser
    130                     135                     140

Glu Leu Gly Asp Leu Asp Thr Trp Gln Glu Asn Thr Asn Ala Trp Glu
145                     150                     155                     160

Glu Glu Glu Asp Ala Ala Trp Gln Ala Glu Glu Val Leu Arg Gln Gln
                165                     170                     175

Lys Leu Ala Asp Arg Glu Lys Arg Ala Ala Glu Gln Gln Arg Lys Lys
                180                     185                     190

Met Glu Lys Glu Ala Gln Arg Leu Met Lys Lys Glu Gln Asn Lys Ile
        195                     200                     205

Gly Val Lys Leu Ser
        210
```